United States Patent
Punyani et al.

(10) Patent No.: US 11,782,052 B2
(45) Date of Patent: *Oct. 10, 2023

(54) BIOSENSOR FOR MALE INFERTILITY

(71) Applicant: Spermosens AB, Lund (SE)

(72) Inventors: Kushagr Punyani, Malmo (SE); Sudha Srivastava, New Delhi (IN); Mohamad Takwa, Lund (SE)

(73) Assignee: Spermosens AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/492,331

(22) Filed: Oct. 1, 2021

(65) Prior Publication Data

US 2022/0026413 A1    Jan. 27, 2022

Related U.S. Application Data

(63) Continuation of application No. 17/260,609, filed as application No. PCT/EP2019/072574 on Aug. 23, 2019.

(30) Foreign Application Priority Data

Aug. 24, 2018 (EP) .................................... 18190720

(51) Int. Cl.
    G01N 33/50    (2006.01)
    G01N 27/327   (2006.01)
    G01N 33/543   (2006.01)
    G01N 33/68    (2006.01)

(52) U.S. Cl.
    CPC ..... G01N 33/5044 (2013.01); G01N 27/3277 (2013.01); G01N 33/5438 (2013.01); G01N 33/689 (2013.01)

(58) Field of Classification Search
    CPC ........... G01N 33/5044; G01N 33/5438; G01N 33/689
    See application file for complete search history.

(56) References Cited

U.S. PATENT DOCUMENTS

| 6,649,419 B1* | 11/2003 | Anderson ............... B03C 1/284 436/805 |
| 2003/0148930 A1 | 8/2003 | Chi |
| 2011/0111452 A1 | 5/2011 | Zanbar |
| 2014/0057310 A1 | 2/2014 | Fang |
| 2015/0297552 A1* | 10/2015 | Roziev ............... A61K 47/6951 536/103 |
| 2016/0313246 A1* | 10/2016 | Wong ................... G01N 21/553 |
| 2017/0219554 A1* | 8/2017 | Lee ..................... G01N 33/5438 |

FOREIGN PATENT DOCUMENTS

| CN | 106033086 A | 10/2016 |
| WO | 1999042581 | 8/1999 |
| WO | 2003011118 | 2/2003 |
| WO | 2008026906 | 3/2008 |
| WO | 2013012749 | 1/2013 |
| WO | 2013122265 | 8/2013 |

OTHER PUBLICATIONS

Yanase et al. "Surface Plasmon Resonance for Cell-Based Clinical Diagnosis" (Sensors 2014 14:4948-4959). (Year: 2014).*
Grayson (Royal Society Open Science 2015 vol. 2: 150296) (Year: 2015).*
Campbell ("Monoclonal Antibody Technology", Elsevier Sci Pub. 1984, total 15 pages) (Year: 1984).*
Kerr (J. Visualized Experiments 2012 61: e3881). (Year: 2012).*
Agarwal et al., "A unique view on male infertility around the globe", Apr. 26, 2015, p. 37, vol. 13, Publisher: Reprod Biol Endocrinol.
Aydin et al., "Molecular architecture of the human sperm IZUMO1 and egg JUNO fertilization complex", Jun. 23, 2016, pp. 562-565, vol. 534, No. 7608, Publisher: Nature.
Bianchi et al., "Juno is the egg Izumo receptor and is essential for mammalian fertilization", Apr. 24, 2014, pp. 483-487, vol. 508, No. 7497, Publisher: Nature.
Bianchi et al., "Cross-species fertilization: the hamster egg receptor, Juno, binds the human sperm ligand, Izumo1", Feb. 2015, p. 20140101, vol. 370, No. 1661, Publisher: Philos Trans R Soc Lond B Biol Sci.
Eshre Special Interest Group of Embryology; Alpha Scientists in Reproductive Medicine, "The Vienna consensus: report of an expert meeting on the development of art laboratory performance indicators", Aug. 4, 2017, pp. 1-17, vol. 2017, No. 2, Publisher: Hum Reprod Open.
Georgadaki et al., "The molecular basis of fertilization (Review)", Oct. 2016, pp. 979-986, vol. 38, No. 4, Publisher: Int J Mol Med.
Liu & Baker, "Disordered zona pellucida-induced acrosome reaction and failure of in vitro fertilization in patients with unexplained infertility", Jan. 2003, pp. 74-80, vol. 79, No. 1, Publisher: Fertil Steril.
Liu & Baker, "Defective sperm-zona pellucida interaction: a major cause of failure of fertilization in clinical in-vitro fertilization", Mar. 2000, pp. 702-708, vol. 15, No. 3, Publisher: Hum Reprod.
Oehninger S, "Biochemical and functional characterization of the human zona pellucida", Dec. 2003, pp. 641-648, vol. 7, No. 6, Publisher: Reprod Biomed Online.
Ohto et al., "Structure of IZUMO1-JUNO reveals sperm-oocyte recognition during mammalian fertilization", Jun. 2016, pp. 566-569, vol. 534, No. 7608, Publisher: Nature.

(Continued)

*Primary Examiner* — Changhwa J Cheu

(74) *Attorney, Agent, or Firm* — Dinsmore & Shohl LLC; Weston R. Gould

(57) ABSTRACT

The present invention relates to a biosensor and applications thereof for the quantification of sperm function. Methods and tools for diagnosis of male infertility are also disclosed herein.

20 Claims, 13 Drawing Sheets

Specification includes a Sequence Listing.

(56) References Cited

OTHER PUBLICATIONS

Raj et al., "Structural Basis of Egg Coat-Sperm Recognition at Fertilization", Jun. 15, 2017, pp. 1315-1326e17, vol. 169, No. 7, Publisher: Cell.
Talwar & Hayatnagarkar, "Sperm function test", Apr. 1, 2015, pp. 61-69, vol. 8, No. 2, Publisher: J Hum Reprod Sci.
Yu et al., "Mutational analysis of IZUMO1R in women with fertilization failure and polyspermy after in vitro fertilization", Mar. 2018, pp. 539-544, vol. 35, No. 3, Publisher: J Assist Reprod Genet.
Office Action received in JP2021507472 dated Sep. 13, 2022.
Office Action received in KR1020217008528 dated Oct. 28, 2022.

* cited by examiner

BIOSENSOR FOR MALE INFERTILITY

CROSS-REFERENCE TO RELATED APPLICATIONS

This application is a continuation of U.S. application Ser. No. 17/260,609, which is herein incorporated by reference in its entirety and is a 371 national phase entry of PCT/EP2019/072574, filed Aug. 23, 2019, which claims priority to EP 18190720.5 filed Aug. 24, 2018.

REFERENCE TO A SEQUENCE LISTING SUBMITTED VIA EFS-WEB

The content of the ASCII text file of the sequence listing named "20211001_310363_001CON1_ST25" which is 20.6 kb in size was created on Oct. 1, 2021 and electronically submitted via EFS-Web herewith the application is incorporated herein by reference in its entirety.

TECHNICAL FIELD

The present invention relates to a biosensor and applications thereof for the quantification of sperm function and evaluation of male fertility.

BACKGROUND

Around 15% of the global population is affected by infertility, wherein male infertility is known to contribute to 20-70% of all the cases (Reprod Biol Endocrinol. 2015, 13:37). It has further been estimated that 2.5-12% of all men are infertile. With the declining birth rates, and other male infertility-associated factors in Europe, the situation is alarming. As treatment of male infertility relies on accurate diagnosis, the analysis and detection of the underlying cause is critical. Besides anatomical and endocrine analyses, current trends in laboratory diagnosis of male infertility span sperm and semen characteristics (Mayo Clinic). 30-40% of the cases of male infertility are related to unknown male infertility-associated factors (European Association of Urology, 2015). This is known as idiopathic male infertility, treatment of which calls for exploring detailed functional analyses.

Further, Assisted Reproductive Technology (ART) is a standard treatment option that also encounters this roadblock. In 2015, 1.6% of all infants in U.S. were conceived via ART. Although 231,936 ART cycles were performed in U.S. in 2015 alone, they led to 60,778 live births (Centers for Disease Control and Prevention, 2016). In 2017, the European Society of Human Reproduction and Embryology identified failed fertilization rate (FFR) of the oocyte after regular In Vitro Fertilization (IVF) as a Key Performance Indicator for ART labs, with a very low competence level of 5% (Human Reprod Open. 2017, 2). It is important to note that while sperm morphology cannot be correlated to IVF success/failure, failure of fertilization is attributed to issues with sperm function (Human Reprod. 2000, 15(3): 702; Fertil Steril. 2003 January; 79(1):74). Thus there is a need for development of a robust method for diagnosing the fertilization competence of sperm cells in order to predict the viability of IVF, and better select the appropriate ART method.

Before ART, typically male-infertility-associated factors are probed and include sperm quality analysis, sperm counts, concentration, morphology and motility, identification of atypical cell types in semen, and presence of autoimmune antibodies. Additional analyses may involve studying the interaction of sperm cells with cervical mucus, acrosomal reaction, biochemical assays for accessory sex organ function, and estimation of reactive oxygen species and DNA damage (World Health Organization, 2010). In cases of idiopathic male infertility and failure of fertilization in IVF, these values do not provide much information on the underlying cause of infertility. Resorting to intracytoplasmic sperm injection (ICSI) is most often the preferred methodology, but the unnecessary step of IVF leads to wastage of healthy oocytes and financial load.

While the morphological and kinetic properties of sperm cells are crucial for fertilization in vivo or in IVF, the ultimate step in fertilization is the fusion of sperm cells with the ovum. Research methods like Hemizona assay, Human sperm-oocyte interaction test and Human zona pellucida binding test can mimic parts of this step. However, these methods cannot be commercialized due to their reliance on human oocytes, or parts thereof, which are not readily available. Zona-free hamster oocyte penetration test was developed for the purpose of using hamster oocytes instead of human oocytes. While the test negates the requirement for human oocytes, it has a poor predictive value for the success of fertilization in IVF treatment at any insemination concentration, and the usage of this test is therefore significantly limited.

The primary binding between the two gametes is mediated by the extracellular layer of Zona pellucida (ZP) glycoproteins surrounding the ova (Cell. 2017, 169(7):1315; Reprod Biomed Online. 2003, 7(6):641). This interaction is responsible for triggering the acrosomal reaction in sperm cells. Further, sperm cells that have not commenced acrosomal reaction prior to encountering ZP are not able to fertilize the ova. Next, the hydrolases released from the acrosome need to digest the ZP, thereby permitting the sperm to make its way to the ova membrane.

The crucial step in this binding was discovered in 2014. The sperm surface antigen IZUMO1 binds to the female counterpart JUNO protein, formerly known as Folate receptor 4 (Nature. 508: 483-487; Nature. 2016, 534(7608):566). This biochemical event has been discovered to be essential for fusion of the two gametes. Any biochemical mismatch may lead to failure of fertilization.

Hence, being able to quantify the amount of sperm cells in a semen sample capable of binding to the JUNO protein is important in the evaluation of fertility.

A biosensor is a sensor that utilizes the molecule-identifying function of a biological material, e.g. a microorganism, enzyme, antibody, DNA, and RNA, and applies such a biological material as a molecule-identifying element. In other words, the biosensor utilizes the reaction occurring when an immobilized biological material identifies a target substrate, oxygen consumed by breathing of microorganism, enzyme reaction, luminescence, and the like. Among biosensors, practical use of enzyme sensors is developing. For example, enzyme sensors for glucose, lactic acid, uric acid, and amino acids find applications in medical instrumentation and food processing industry.

Different techniques may be used to follow the interaction between for example a protein bound to an electrode and the target species, such as the sperm. One of such techniques relies on Surface Plasmon Resonance (SPR). In SPR, one molecular partner, such as a protein, is immobilized on a metal (the chip). Light excites surface plasmons in the metal; when the binding partner binds to the immobilized molecule, this causes a detectable change in the surface plasmon signal. Another of such techniques relies on electrochemical transduction in which the content of a biological sample is analyzed by the direct conversion of a biological event to an electronic signal. The most common techniques in electrochemical biosensing comprise cyclic voltammetry, chronoamperometry, chronopotentiometry, impedance spectroscopy, and field-effect transistor based methods along with nanowire or magnetic nanoparticle-based biosensing.

SUMMARY

The present inventors utilize the biochemical reaction between the JUNO protein and the sperm surface antigen IZUMO1 in order to discern the fertilization potential of sperm cells. Besides revealing the underlying cause of infertility, this will especially be useful for selection of suitable ART techniques, i.e. a choice between regular IVF and ICSI, while minimizing the wastage of ova. The present inventors further propose development and clinical validation of an electrochemical and/or optical sensing platform(s) that probes the fertilization potential of sperm cells in order to diagnose male infertility. The existing commercial methods to diagnose male infertility and check the sperm quality look into physical aspects of the sperm cells, while overlooking the biochemical interaction that is necessary for the fertilization event. The proposed method has advantages over the existing diagnostic methods, as it is the first bioinspired assay for male fertility analysis that exploits bioreceptors of sperm cells, and it mimics crucial steps of fertilization by the sperm cells thereby giving a direct insight into their fertilization potential. Previously, sperm-oocyte interaction tests have been developed, but they all either require using human oocytes and zona pellucidae, which are not easily available, or they are unreliable due to having a low correlation between the test results and the various semen parameters. The present invention overcomes the problem of oocytes availability by creating conditions that mimic the oocyte and in particular by using one or more of the crucial protein receptors involved in sperm-oocyte fusion.

It is an aspect of the present disclosure to provide a biosensor for quantification of sperm function, the biosensor comprising a substrate and a JUNO protein or a fragment thereof, wherein the JUNO protein or fragment thereof is immobilized on the substrate.

It is a further aspect of the present disclosure to provide a biosensor for detection of sperm function, the biosensor comprising a substrate and a JUNO protein or a fragment thereof, wherein the JUNO protein or fragment thereof is immobilized on the substrate.

It is also an aspect of the present disclosure to provide a method for detecting and/or quantifying sperm function, wherein the method comprises the steps of:
  a. Providing a semen sample from a subject, wherein said semen sample comprises one or more sperm cells,
  b. Contacting the semen sample with the biosensor according to any one of the preceding claims,
  c. Determining binding of the sperm cells to a protein immobilized on the sensor,
  thereby detecting and/or quantifying the sperm function of said sample.

It is also an aspect of the present disclosure to provide a method for diagnosis of male infertility, wherein the method comprises the steps of:
  a. Providing a semen sample from a subject,
  b. Contacting the semen sample with the biosensor according to the present disclosure,
  c. Quantifying the sperm function of said sample according to the method of the present disclosure,
  d. Using the sperm function to diagnose if the subject is infertile.

It is also an aspect of the present disclosure to provide a method for diagnosis of male infertility, wherein the method comprises the steps of:
  a. Providing a sperm sample from a subject,
  b. Contacting the sperm sample with the biosensor according to the present disclosure,
  c. Quantifying the sperm function of said sample according to the method of the present disclosure,
  d. Using the sperm function to diagnose if the subject is infertile.

Another aspect of the present disclosure is the provision of a method for manufacturing a biosensor comprising a JUNO protein, the method comprising:
  a. Providing a substrate,
  b. providing the JUNO protein,
  c. immobilizing the JUNO protein on the substrate,
  thereby manufacturing a biosensor comprising the JUNO protein.

It is a further aspect of the present disclosure to provide a method of selecting sperm, said method comprising:
  a. Providing a semen sample from a subject, wherein said semen sample comprises one or more sperm cells,
  b. Contacting the semen sample with the biosensor according to the present disclosure,
  c. Visualizing a sperm bound to the biosensor by microscopy,
  thereby selecting said sperm.

It is a further aspect of the present disclosure to provide a method of selecting sperm, said method comprising:
  a. Providing a sperm sample from a subject,
  b. Contacting the sperm sample with the biosensor according to the present disclosure,
  c. Visualizing a sperm bound to the biosensor by microscopy,
  thereby selecting said sperm.

It is also an aspect of the present disclosure to provide a hand-held device for detection and/or quantification of sperm function, the device comprising:
  a. An inlet for a sample;
  b. A biosensor comprising a JUNO protein or a fragment thereof, wherein the JUNO protein is immobilized on the biosensor, and wherein the inlet is configured to place the sample in contact with the sensor;
  c. A detector configured to receive a signal from the sensor and transform it into a format readable by a user;
  d. Optionally, means for separating cellular components from the sample.

DETAILED DESCRIPTION

Figure 1:
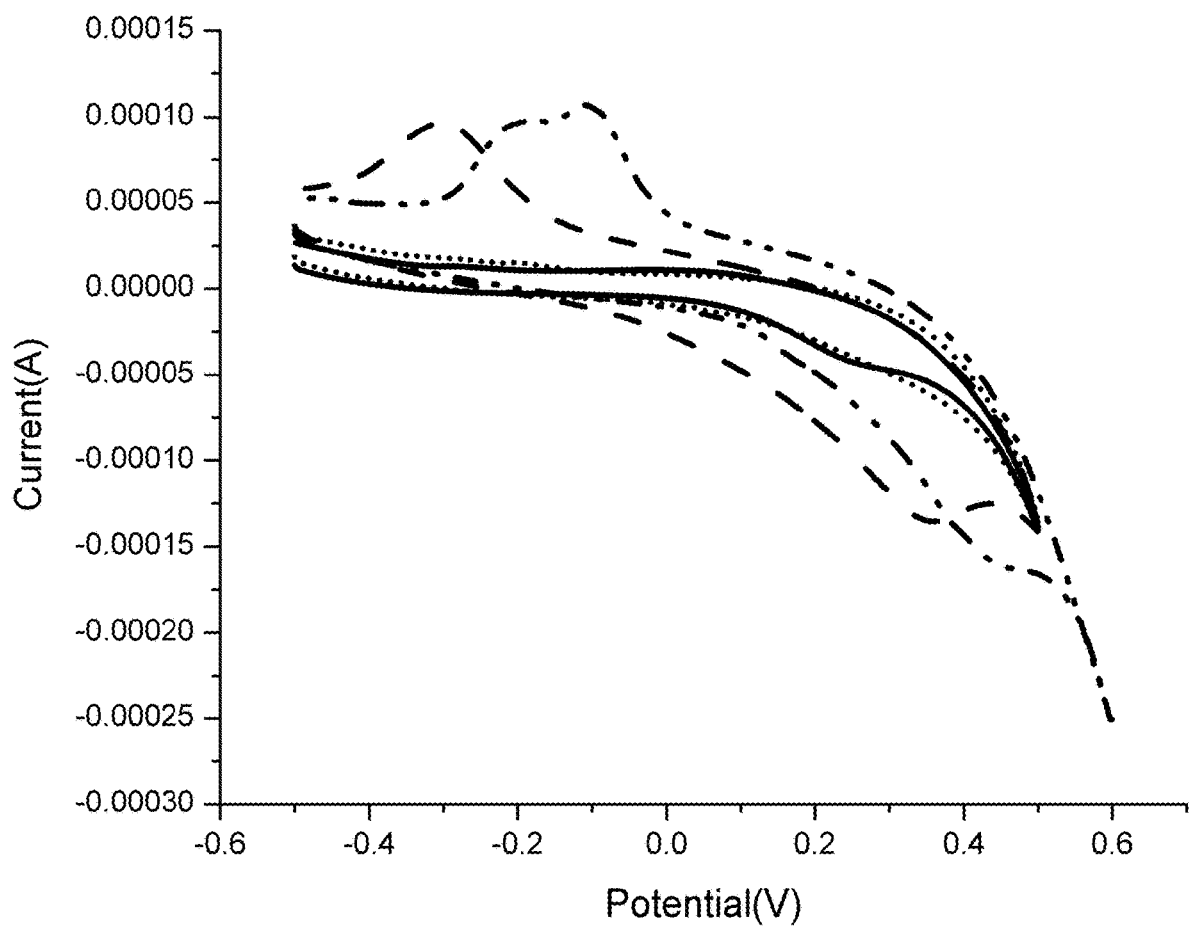
FIG. 1: Cyclic voltammetric response of a) Electrode-gold nanoparticles-BSAblocking after addition of buffer only (solid line) and after addition of semen sample diluted $1.67 \times 10^{-2}$X in buffer (dotted line) b) Electrode-gold nanoparticles-JUNO-BSAblocking (dash dot dot line) and c) Electrode-gold nanoparticles-ZP3-BSAblocking response (dashed line) after addition of semen sample diluted $1.67 \times 10^{-2}$X in buffer, with the dilution factor given by the initial volume/final volume.
Figure 2A:
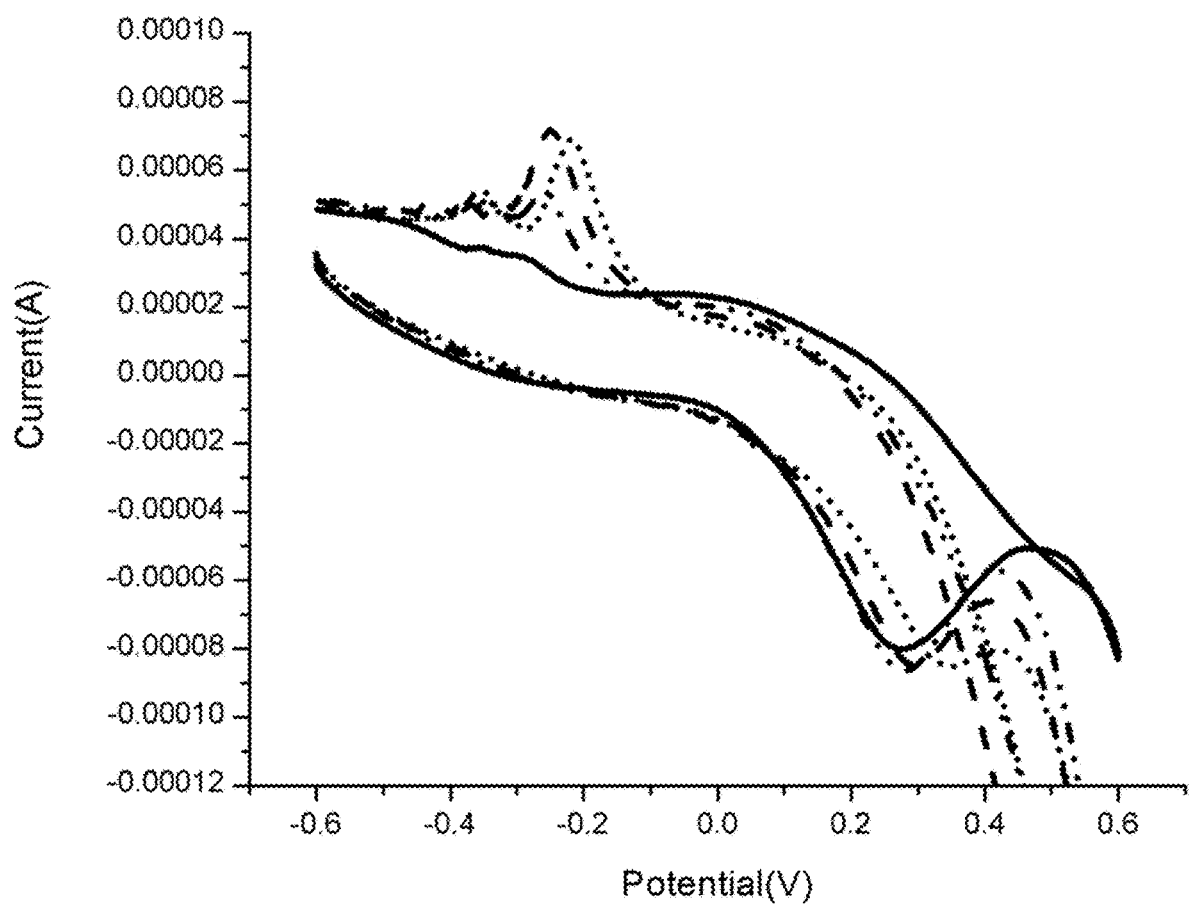
FIG. 2A to FIG. 2F: Cyclic voltammetric response of Electrode-gold nanoparticles-ZP3-BSAblocking after addition of three different dilutions ($1.56 \times 10^{-5}$X (dotted line), $1.67 \times 10^{-2}$X (dash dot dot line) and $2.5 \times 10^{-2}$X (dashed line)) of 6 different semen samples (FIG. 2A-FIG. 2F), while solid line shows electrode response with buffer only (no semen sample).
Figure 2B:
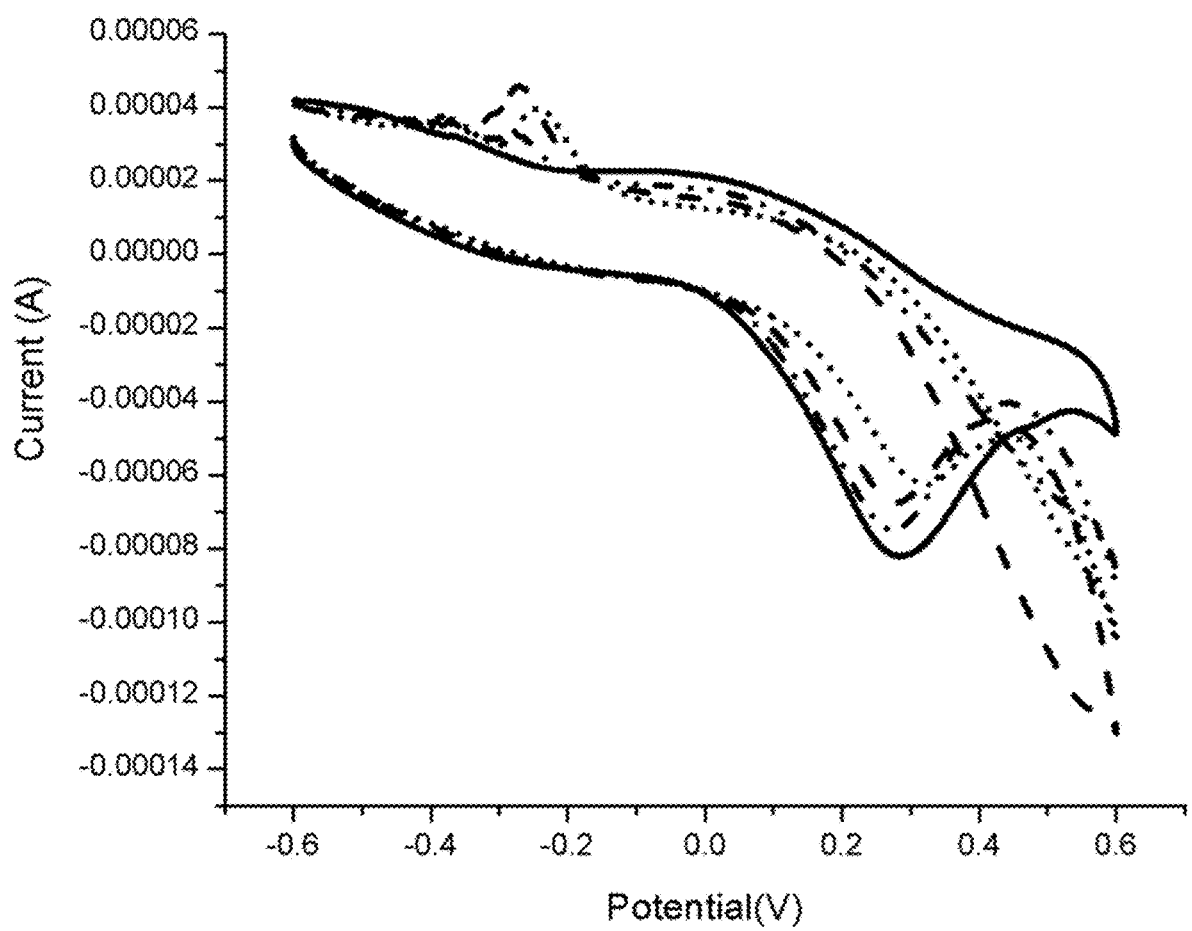
Figure 2C:
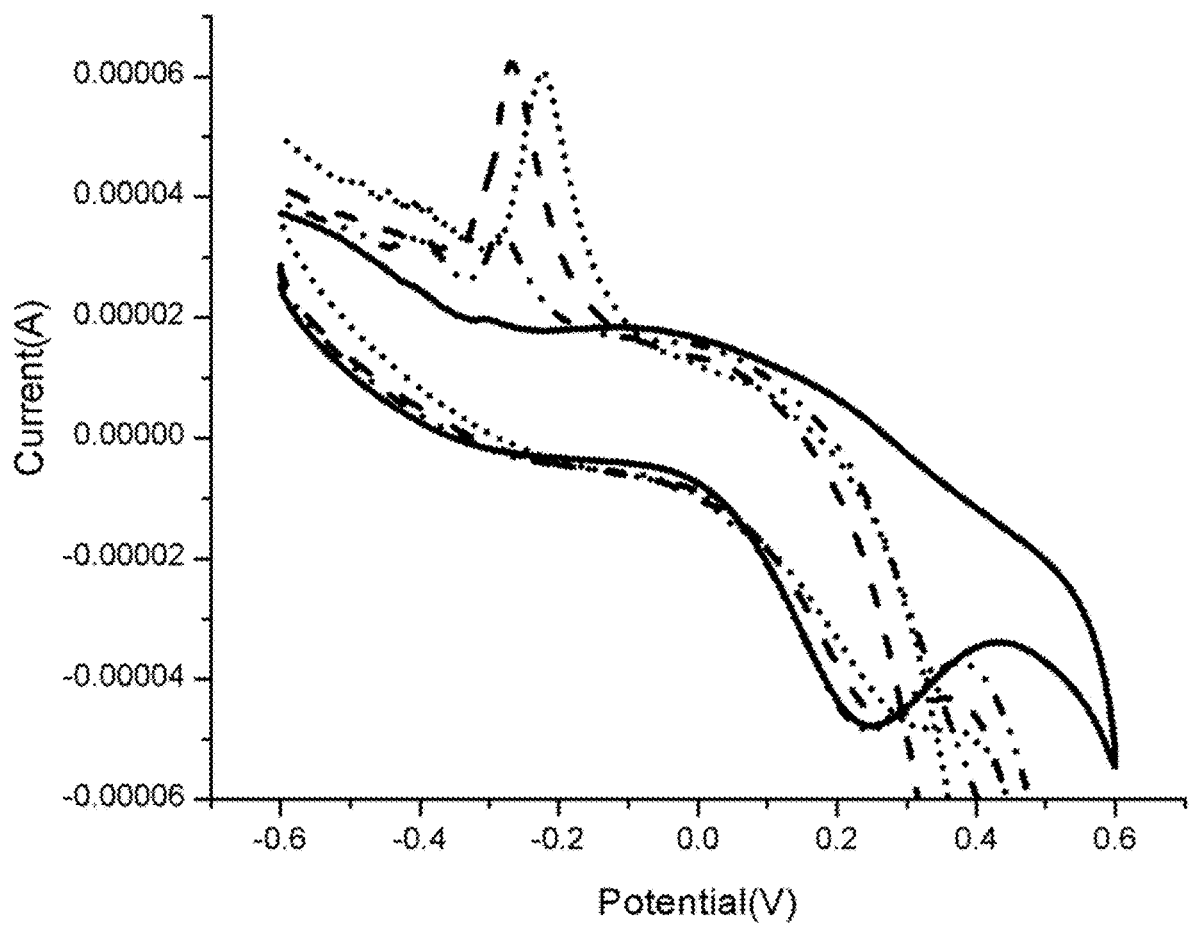
Figure 2D:
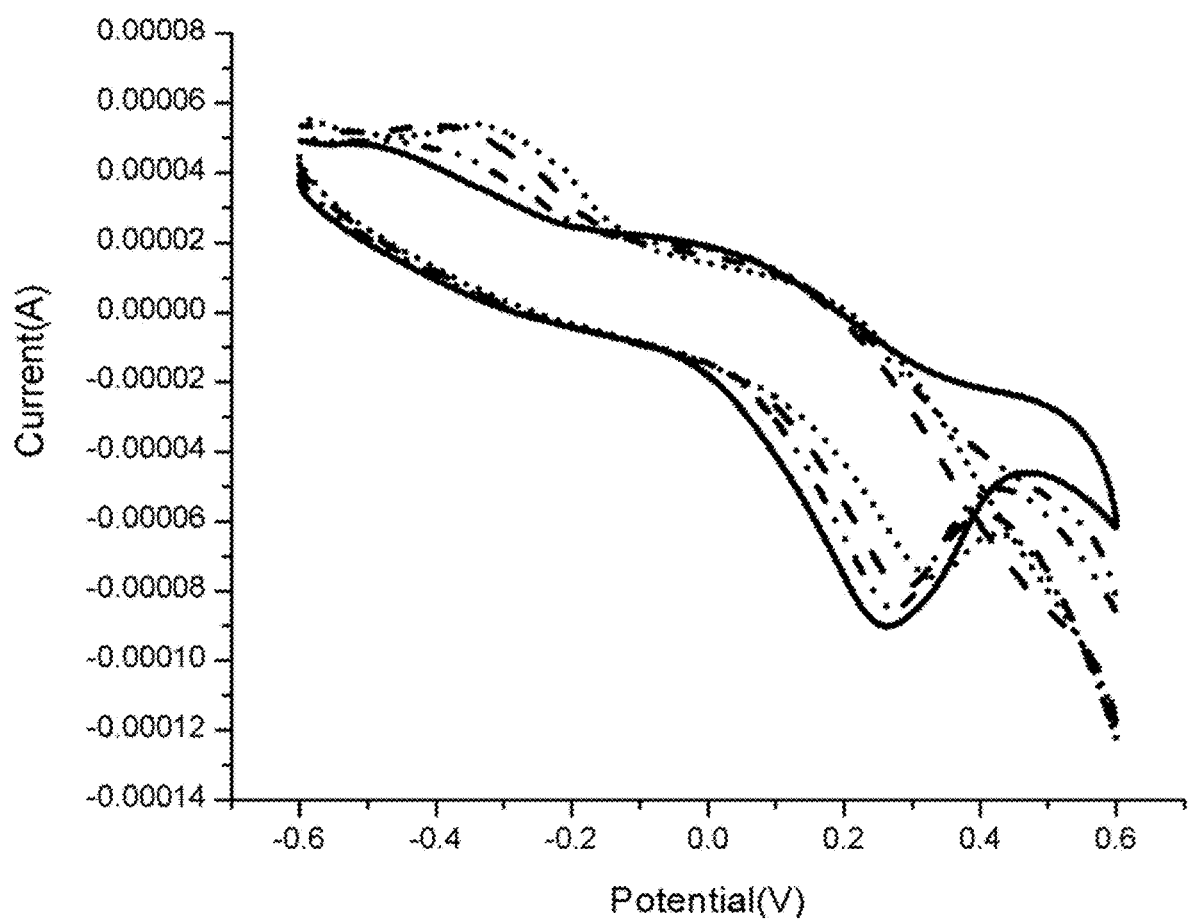
Figure 2E:
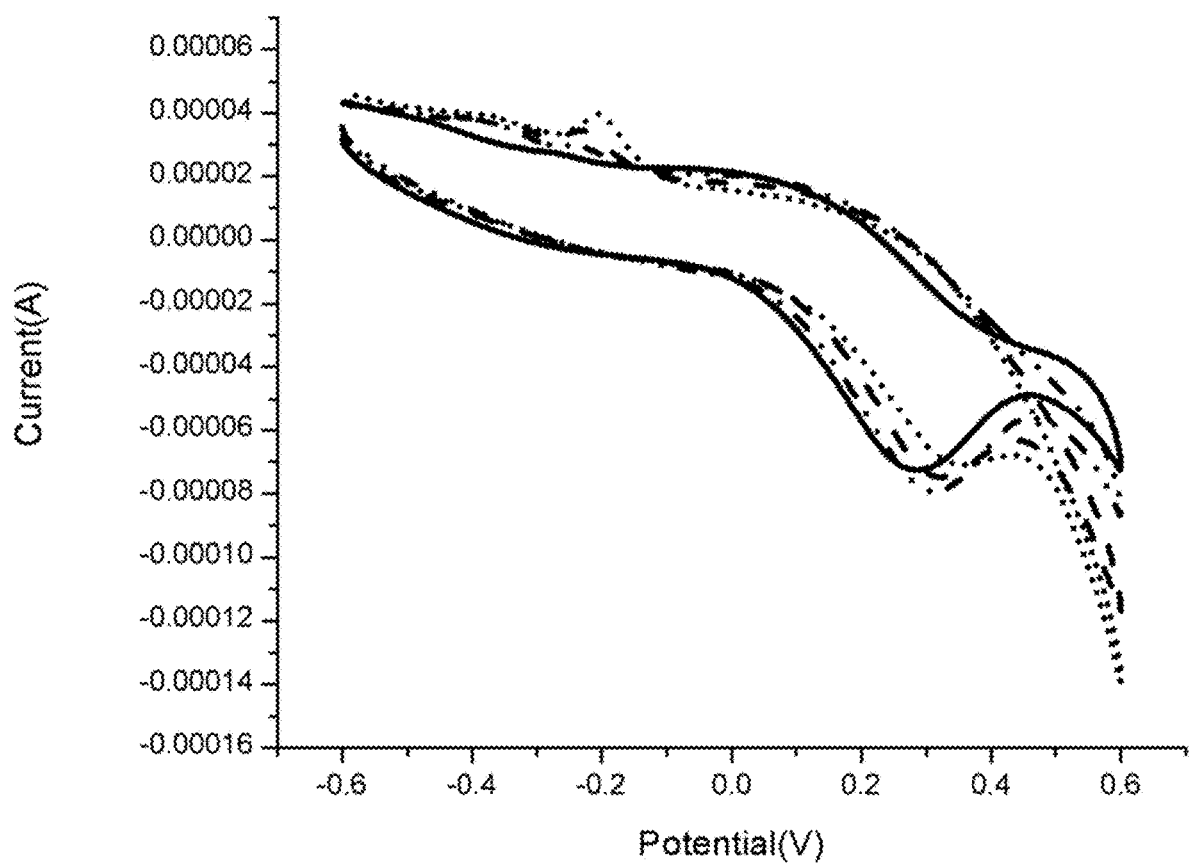
Figure 2F:
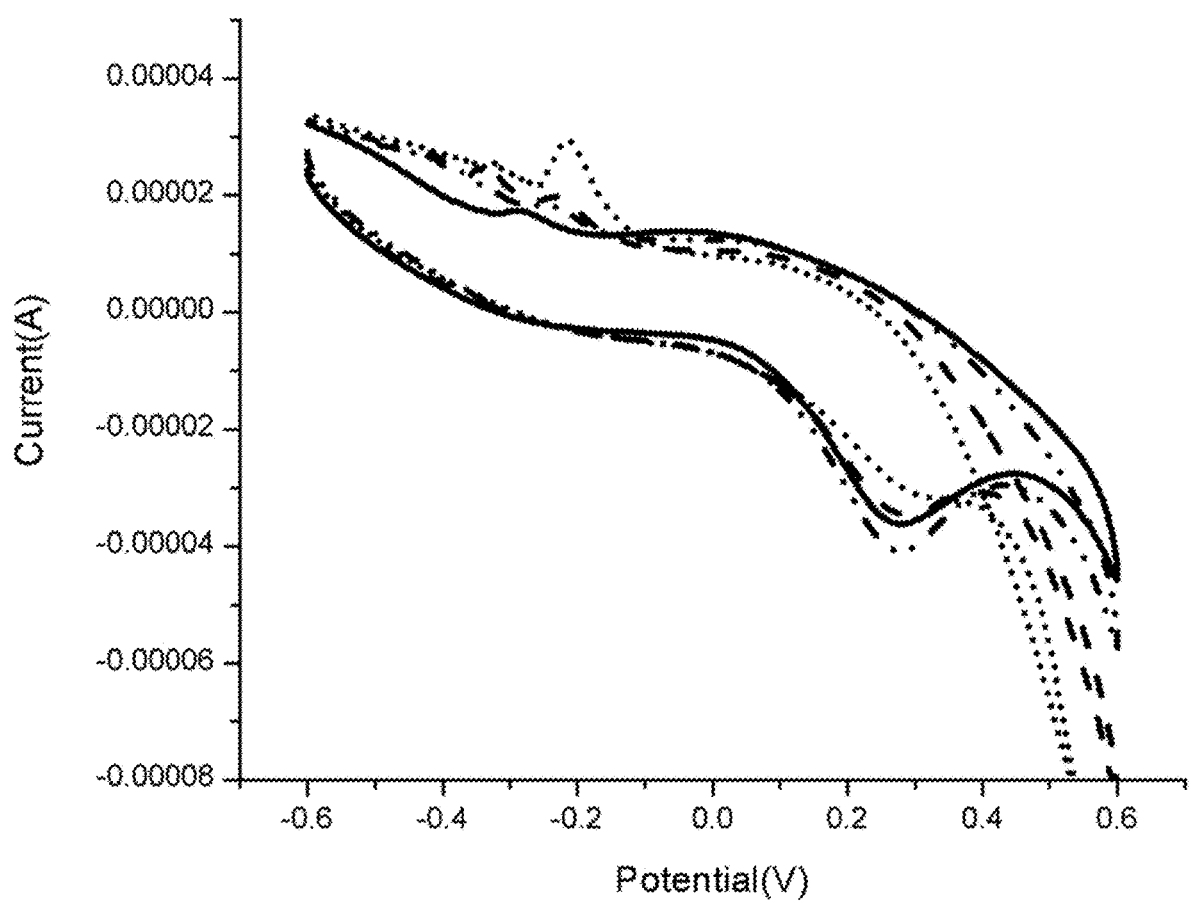
Figure 3A:
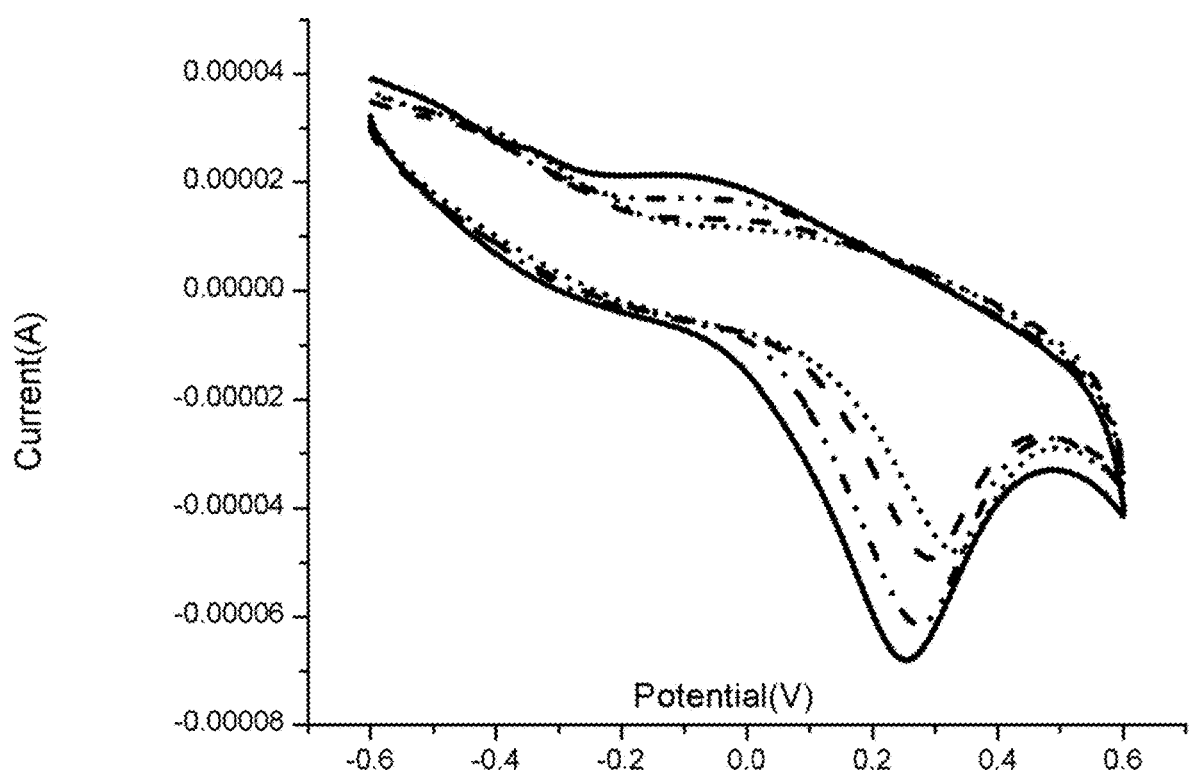
FIG. 3A to FIG. 3F: Cyclic voltammetric response of Electrode-gold nanoparticles-JUNO-BSAblocking after addition of three different dilutions ($1.56 \times 10^{-5}X$ (dotted line), $1.67 \times 10^{-2}X$ (dash dot dot line) and $2.5 \times 10^{-2}X$ (dashed line)) of semen samples S1, S2, S3, S4, S5 and S6 (FIG. 3A-FIG. 3F, respectively), while solid line shows electrode response with buffer only (no semen sample).
Figure 3B:
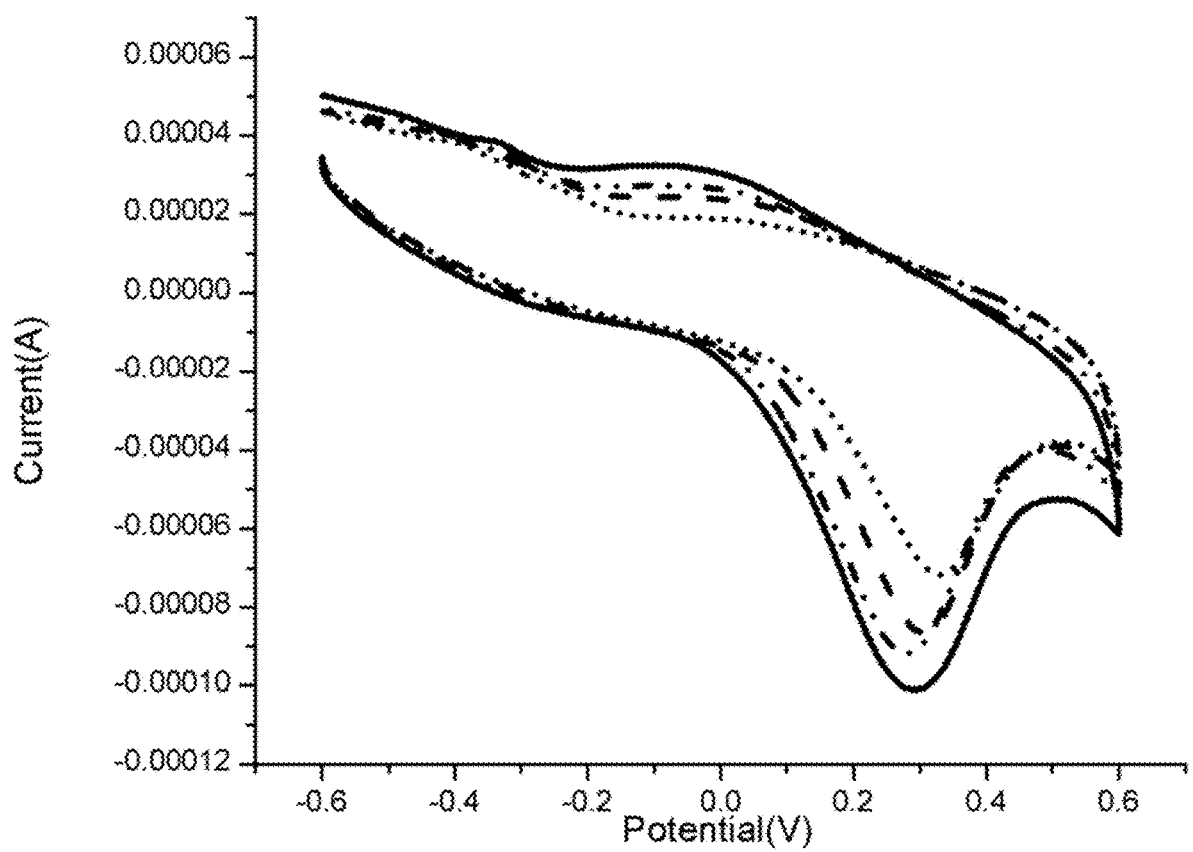
Figure 3C:
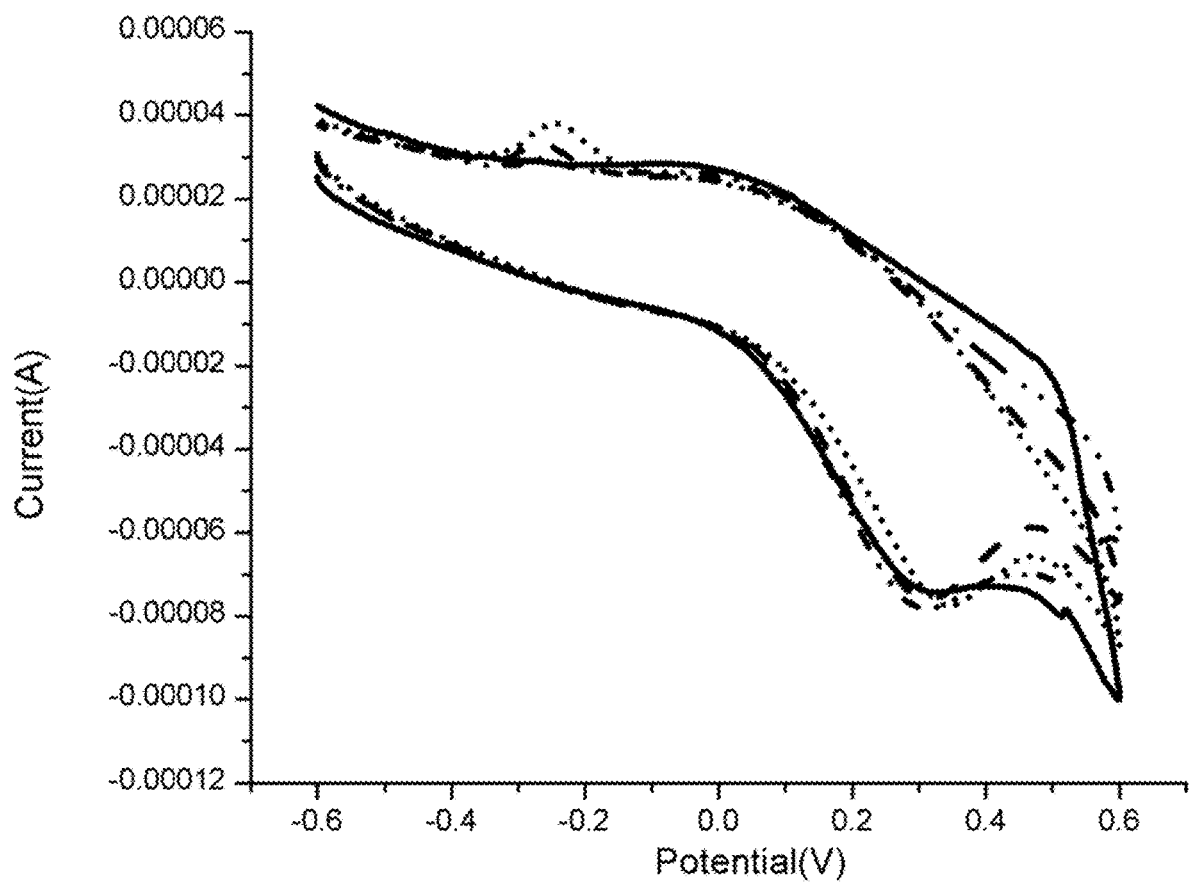
Figure 3D:
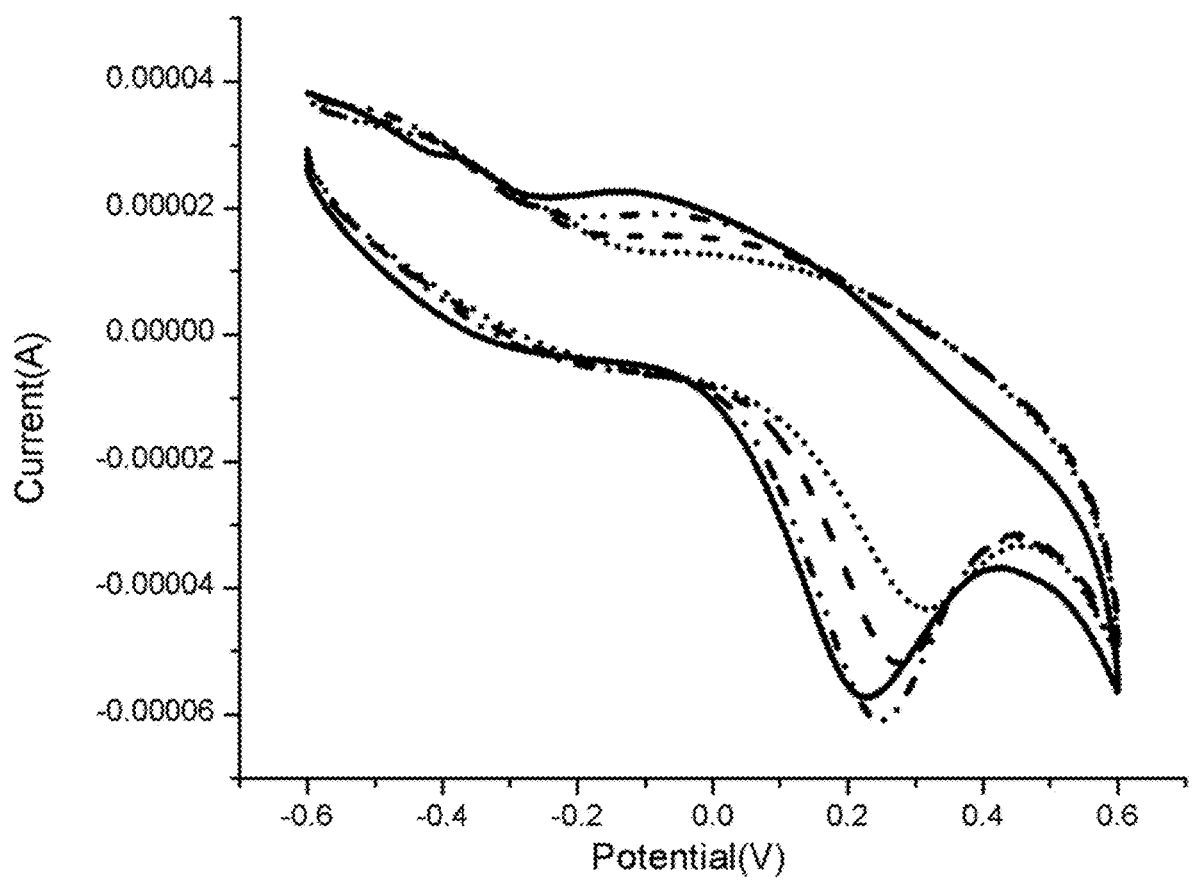
Figure 3E:
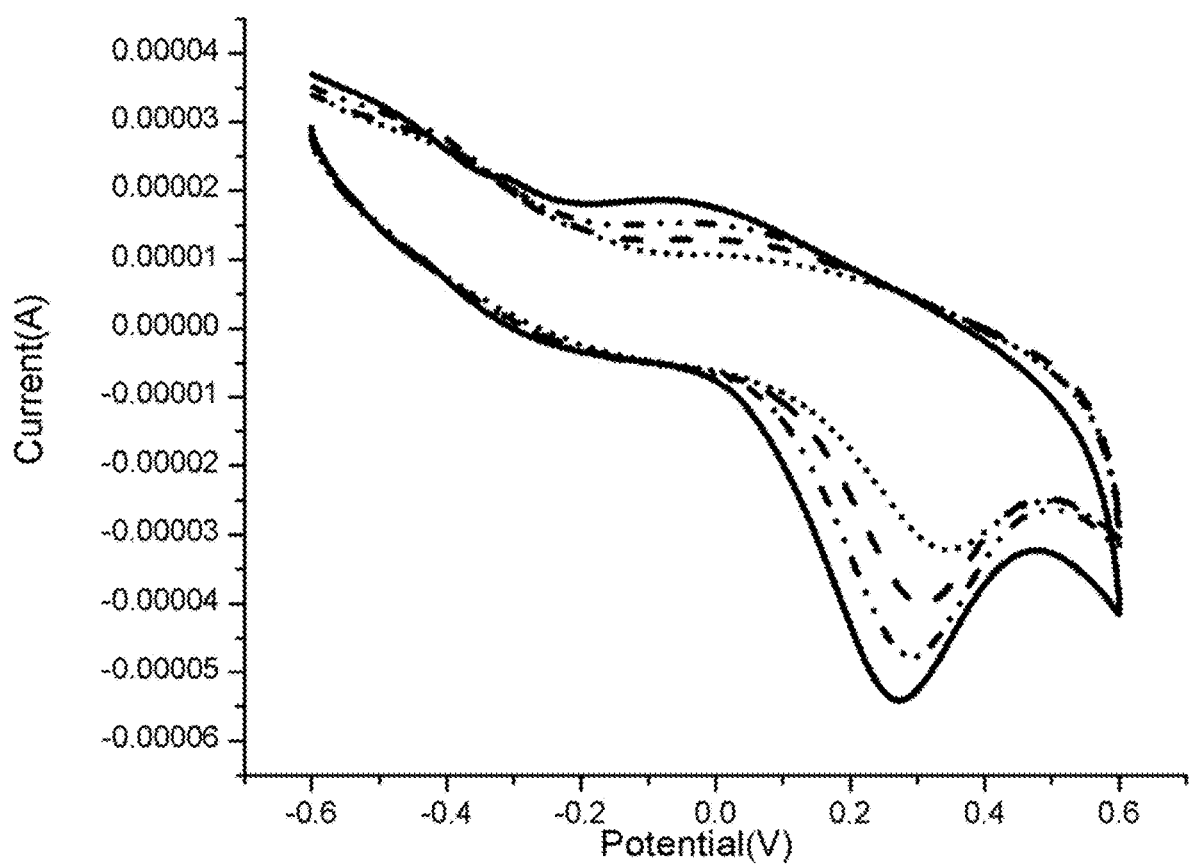
Figure 3F:
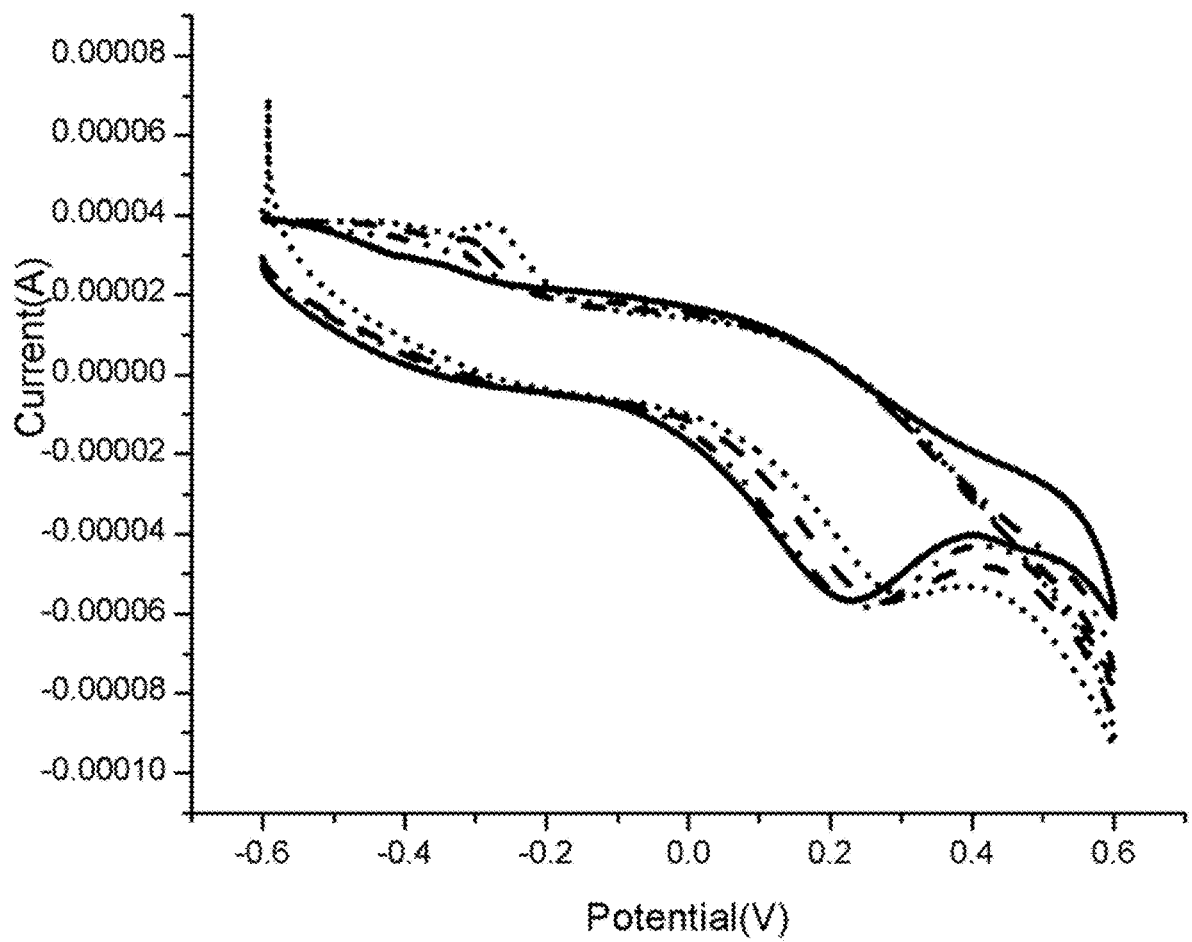

Disclosed herein is a biosensor and applications thereof for the quantification of sperm function to evaluate male infertility. Further, the present disclosure relates to methods for diagnosis of infertility in a subject comprising determining the sperm function of sperm cells in a sample obtained from said subject.

Sperm Function

The main function of sperm is to reach the ovum to induce fertilization by fusing with it to deliver two sub-cellular structures: (i) the male pronucleus that contains the genetic material and (ii) the centrioles that are structures that help organize the microtubule cytoskeleton. Hence, sperm function can be understood as the sperm's ability to reach the ovum and induce fertilization.

The primary binding between the two gametes is mediated by the extracellular layer of Zona pellucida (ZP) glycoproteins surrounding the ova (Cell. 2017, 169(7):1315; Reprod Biomed Online. 2003, 7(6):641). This interaction is responsible for triggering the acrosomal reaction in sperm cells. Further, sperm cells that have not commenced acrosomal reaction prior to encountering ZP are not able to fertilize the ova. Next, the hydrolases released from the acrosome need to digest the ZP, thereby permitting the sperm to make its way to the ova membrane.

The crucial step in this binding was discovered in 2014. The sperm surface antigen IZUMO1 binds to the female counterpart JUNO protein, formerly known as Folate receptor 4 (Nature. 508: 483-487; Nature. 2016, 534(7608):566). This biochemical event has been discovered to be essential for fusion of the two gametes.

The present disclosure is directed to a biosensor for quantification of sperm function, the biosensor comprising a substrate and a JUNO protein or a fragment thereof, wherein the JUNO protein or fragment thereof is immobilized on the substrate. In fact, probing sperm function through binding of sperm cells to a biosensor comprising the JUNO protein may be a viable strategy, and may ultimately allow diagnosis of male infertility, that overcomes the need for human or animal oocytes or parts thereof.

In some embodiments, a biosensor according to the present disclosure is provided, wherein the sperm function is determined from the binding of at least a portion of sperm to a protein, or a fragment thereof, which has been immobilized on the sensor, wherein said protein(s) is JUNO protein, ZP1, ZP2, ZP3 and/or an anti-IZUMO antibody, or fragments thereof. In some embodiments, the at least a portion of sperm comprises an IZUMO1 surface antigen.

It is an aspect of the disclosure to provide a method for detecting and/or quantifying sperm function, wherein the method comprises the steps of:
 a. Providing a semen sample from a subject, wherein said semen sample comprises one or more sperm cells,
 b. Contacting the semen sample with the biosensor according to any one of the preceding claims,
 c. determining binding of the sperm cells to a protein immobilized on the sensor,
thereby detecting and/or quantifying the sperm function of said sample.

It is a further aspect of the present disclosure to provide a method for diagnosis of male infertility, wherein the method comprises the steps of:
 a. Providing a semen sample from a subject,
 b. Contacting the semen sample with the biosensor according to the present disclosure,
 c. Quantifying the sperm function of said sample according to the method disclosed herein,
 d. Using the sperm function to diagnose if the subject is infertile.

It is another aspect of the present disclosure to provide a method for diagnosis of male infertility, wherein the method comprises the steps of:
 a. Providing a sperm sample from a subject,
 b. Contacting the sperm sample with the biosensor according to the present disclosure,
 c. Quantifying the sperm function of said sample according to the method disclosed herein,
 d. Using the sperm function to diagnose if the subject is infertile.

The term "sperm function" as used herein refers to the sperm health, which is the ability a sperm to capacitate and to fertilize an egg. Sperm function tests are diagnostic or research methods that probe the biochemical or molecular traits of sperm cells. The following reference has several examples of sperm function tests: Talwar and Hayatnagarkar 2015. J Hum Reprod Sci. 8(2): 61-69. The present disclosure relates to sperm function tests which are also referred to as sperm-oocyte interaction tests, wherein the tests, instead of using an oocyte, mimic the conditions of sperm-oocyte interaction by using one or more of the crucial protein receptors involved in sperm-oocyte fusion.

In one embodiment according to the method of the present disclosure, the semen sample comprises, or is suspected of comprising, one or more sperm cells.

In one embodiment according to the method of the present disclosure, the sperm function of said sample is detected by determining binding of the sperm cells to a protein immobilized on the sensor, wherein said protein is selected from the group consisting of JUNO protein, ZP1, ZP2, ZP3 and/or the anti-IZUMO antibody, or fragments thereof, and wherein said binding is detected by microscopic analysis, electrochemical detection and/or surface plasmon resonance.

In one embodiment according to the method of the present disclosure, the sperm function of said sample is quantified by determining binding of the sperm cells to a protein immobilized on the sensor, wherein said protein is selected from the group consisting of JUNO protein, ZP1, ZP2, ZP3 and/or the anti-IZUMO antibody, or fragments thereof, and wherein said binding is detected by microscopic analysis, electrochemical detection and/or surface plasmon resonance.

In one embodiment according to the method of the present disclosure, the sperm function is quantified in step c) by determining the percentage of bound versus unbound sperm cells by microscopic analysis.

In one embodiment according to the method of the present disclosure, the sperm function is quantified in step c) by determining the percentage of bound versus unbound sperm cells by electrochemical detection.

In one embodiment according to the method of the present disclosure, the sperm function is quantified in step c) by determining the percentage of bound versus unbound sperm cells by surface plasmon resonance.

In one embodiment according to the method of the present disclosure, the sperm function is quantified in step c) by determining the acrosomal status of the sperm cells in the semen sample, and/or in the sperm sample, by microscopic analysis.

In one embodiment according to the method of the present disclosure, the sperm function is quantified in step c) by determining the acrosomal status of the sperm cells in the semen sample, and/or in the sperm sample, by electrochemical detection.

In one embodiment according to the method of the present disclosure, the sperm function is quantified in step c by determining the acrosomal status of the sperm cells in the semen sample, and/or in the sperm sample, by surface plasmon resonance.

In one embodiment according to the method of the present disclosure, said method further comprises comparing the percentage of bound versus unbound sperm cells and/or the acrosomal status of the sperm cells with respective reference values, wherein said reference values may be positive reference values (representing functional sperm) and/or negative reference values (representing non-functional sperm). Said reference values may be obtained by testing control semen samples, and/or control sperm samples. Said reference values may also be obtained from data available in the scientific literature.

In one embodiment according to the method of the present disclosure, the sample is treated prior to step b. For example, the semen sample treatment may comprise liquefaction of the sperm. The semen sample treatment may optionally comprise capacitation. The sperm sample treatment may comprise liquefaction of the sperm. The sperm sample treatment may optionally comprise capacitation.

The biosensor disclosed herein may be used to determine sperm function at various levels.

For example, the disclosed biosensor may be used to determine the capability of the sperm cells in the semen sample, and/or in the sperm sample, to bind to the zona pellucidae proteins ZP1, ZP2 and/or ZP3.

The disclosed biosensor may be used to determine the capability of the sperm cells in the semen sample, and/or in the sperm sample, to undergo acrosomal reaction.

Binding to the zona pellucidae proteins ZP1, ZP2 and/or ZP3 is a necessary step for a sperm cell in order to undergo acrosomal reaction. Hence, sperm cells that are not capable of binding to the zona pellucidae proteins ZP1, ZP2 and/or ZP3 will not undergo acrosomal reaction.

Determining whether sperm cells are capable of binding to the zona pellucidae proteins ZP1, ZP2 and/or ZP3 and undergoing acrosomal reaction is important for establishing which assisted reproduction techniques may be used. In particular, sperm cells that are not capable of binding to the zona pellucidae proteins ZP1, ZP2 and/or ZP3 and/or do not undergo acrosomal reaction, may be suitable for IVF, provided that the zona pellucida coat has been removed from the egg.

The disclosed biosensor may be used to determine the capability of the sperm cells in the semen sample, and/or in the sperm sample, to bind a JUNO protein.

A sperm cell may be able to bind a JUNO protein even though said sperm cell is not capable of binding to the zona pellucidae proteins ZP1, ZP2 and/or ZP3, and/or does not undergo acrosomal reaction. This is because the sperm cell may be induced to capacitate and expose surface antigens necessary for binding to the oocyte's cell membrane.

In some embodiments, the sperm function is determined by the ability of a sperm to bind to the immobilized JUNO protein or fragment thereof. Said binding may for example occur via an IZUMO1 protein or fragment thereof situated on the sperm. Said binding may for example occur via an IZUMO1 protein or fragment thereof expressed by the sperm.

In fact, a sperm that has undergone capacitation may present an IZUMO1 protein or fragment thereof on its surface and said IZUMO1 protein or fragment thereof is capable of binding its egg receptor counterpart, for example a JUNO protein or fragment thereof, or an anti-IZUMO antibody or fragment thereof.

In some embodiments, the sperm function is determined by the binding of an IZUMO1 protein or fragment thereof to the immobilized JUNO protein or fragment thereof.

In a particular embodiment, the method according to the present disclosure further comprises a step of treating said male infertility.

In a particular embodiment of the method according to the present disclosure the treatment comprises administration of a medicament in a therapeutically effective amount and/or by artificial reproductive technology (ART). For example, a subject diagnosed with reduced sperm function may undergo reproduction with the help of ART such as intrauterine insemination (IUI), in vitro fertilization (IVF), or IVF with intracytoplasmatic sperm injection (ICSI).

For example, a subject diagnosed with reduced sperm function, in particular with sperm cells characterized by:
A reduced capability of binding to the zona pellucidae proteins ZP1, ZP2 and/or ZP3,
A reduced capability of undergoing acrosomal reaction;
A normal capability of binding a JUNO protein,
may undergo reproduction with the help of IVF.

For example, a subject diagnosed with reduced sperm function, in particular with sperm cells characterized by:
a reduced capability of binding to the zona pellucidae proteins ZP1, ZP2 and/or ZP3,
a reduced capability of undergoing acrosomal reaction;
a reduced capability of binding a JUNO protein,
may undergo reproduction with the help of IVF with ICSI.

The terms "reduced capability" and "normal capability" as used herein are in relation to a reference value, which may be a positive control. The reference value may be obtained by calculating the average values for semen samples of fertile subjects. The reference value may be obtained by calculating the average values for sperm samples of fertile subjects. The reference values may also be obtained from scientific reports. Hence, in order to diagnose a subject with reduced sperm function and/or male infertility, the capability of sperm cells taken from a semen sample, and/or a sperm sample, of said subject of binding to the zona pellucidae proteins ZP1, ZP2 and/or ZP3, and/or of undergoing acrosomal reaction, is compared to at least a reference value, such as a positive control and/or a negative control.

Any treatment for male infertility known to the person skilled in the art may be used.

In some embodiments, the biosensor according to the present disclosure is configured for detection and/or quantification of sperm function.

In one embodiment according to the method of the present disclosure, the sperm function is quantified in step c) by determining the acrosomal status of the sperm cells in the semen sample, and/or in the sperm sample, which results in a translation of the extent of acrosomal reactivity to a measure of sperm function. In a particular embodiment, a fluorophore is added to the sample, followed by a step of analysing said sample by SPR or microscopy to determine the acrosomal status (that is if the sperm cells are "acrosome-reacted") of the sperm cells. In some embodiments, the fluorophore is added to the sample in the inlet of the biosensor only after having contacted said sample with the substrate. In some embodiments, the fluorophore is added to the sample in the inlet of the biosensor only after the acrosomal reaction has occurred. The presence of a fluorophore may facilitate the step of determining the acrosomal status of the sperm cells. For example fluorescently labelled lectins, such as *Pisum sativum* (pea agglutinin) or *Arachis hypogaea* (peanut lectin), or monoclonal antibodies against the acrosome antigen CD46 can be used to assess the acrosomal status of sperm cells. Methods for detecting acrosomal reactions may be found in the WHO laboratory manual for the Examination and processing of human semen, WHO, 5$^{th}$ Edition, 2010, ISBN 978 92 4 154778 9 (see in particular Chapter 4).

In some embodiments according to the method of the present disclosure, the sperm function is quantified in step c) by determining the acrosomal status of the sperm cells in the semen sample, and/or in the sperm sample, which results in a translation of the extent of acrosomal reactivity to a measure of sperm function, wherein the acrosomal reactivity of the semen sample, and/or in the sperm sample, is compared to the average acrosomal reactivity of sperm collected from fertile male individuals, and wherein functional sperm may have acrosomal reactivity equal or higher than the average acrosomal reactivity of sperm collected from fertile male individuals. Data regarding the average acrosomal reactivity of sperm collected from fertile male individuals may be found in the scientific literature and clinical reports.

In some embodiments according to the method of the present disclosure, the sperm function is quantified in step c) by translating the extent of acrosomal reactivity to a measure of sperm function, wherein acrosomal reactivity of 15% or more may be indicative of functional sperm.

In some embodiments according to the method of the present disclosure, the sperm function is quantified in step c) by translating the extent of acrosomal reactivity to a measure of sperm function, wherein acrosomal reactivity of 10% or less may be indicative of non-functional sperm.

In some embodiments according to the method of the present disclosure, the sperm function is quantified in step c) by translating the extent of acrosomal reactivity to a measure of sperm function, wherein acrosomal reactivity of between 10 and 15% may be indicative of abnormal sperm function.

Acrosome Reaction

During fertilization, a sperm must first fuse with the plasma membrane and then penetrate the female egg in order to fertilize it. Prior to penetrating through the egg's hard shell or extracellular matrix, sperm cells undergo a process known as the acrosome reaction. The acrosome reaction is an exocytotic process that occurs after spermatozoa bind to the zona pellucida and must take place before the spermatozoon can penetrate the oocyte vestments and fuse with the oocyte. The acrosome is a cap-like structure over the anterior half of the sperm's head. As the sperm approaches the zona pellucida of the egg, which is necessary for initiating the acrosome reaction, the membrane surrounding the acrosome fuses with the plasma membrane of the sperm's head, exposing the contents of the acrosome. The contents include surface antigens necessary for binding to the egg's cell membrane, and numerous enzymes, which are responsible for breaking through the egg's tough coating and allowing fertilization to occur. For example, the content of the acrosome may comprise an IZUMO1 protein or fragment thereof.

The Biosensor

It is an aspect of the present disclosure to provide a biosensor for quantification of sperm function, the biosensor comprising a substrate and a JUNO protein or a fragment thereof, wherein the JUNO protein or fragment thereof is immobilized on the substrate.

It is also an aspect of the present disclosure to provide a biosensor for detection of sperm function, the biosensor comprising a substrate and a JUNO protein or a fragment thereof, wherein the JUNO protein or fragment thereof is immobilized on the substrate.

In one embodiment, the biosensor according to the present disclosure is a sensor. The sensor or biosensor of the present disclosure is configured for detection and/or quantification of sperm function.

The "biosensor", as used herein is sometimes referred to as a "sensor". A variety of devices for detecting ligand/receptor interactions are known. The most basic of these are purely chemical/enzymatic assays in which the presence or amount of analyte is detected by measuring or quantitating a detectable reaction product. Ligand/receptor interactions can also be detected and quantitated by radiolabel assays.

Quantitative binding assays of this type involve two separate components: a reaction substrate, e.g., a solid-phase test strip, a dish, a chip or an electrode, and a separate reader or detector device, such as a scintillation counter, spectrophotometer, a microscope, or any other detector known in the art. The substrate is generally unsuited to multiple assays, or to miniaturization, for handling multiple analyte assays from a small amount of body-fluid sample.

In biosensors, by contrast, the assay substrate and detector surface may be integrated into a single device. One general type of biosensor employs an electrode surface in combination with current or impedance measuring elements for detecting a change in current or impedance in response to the presence of a ligand-receptor binding event. Another type of biosensor may employ a chip, for example a glass chip, in combination with an optical detector, for example in combination with surface plasmon resonance. Another type of biosensor may employ a dish in combination with a microscope. A further type of biosensor may employ a microbead in combination with an optical or electrical detector, for example suitable for a latex agglutination test. An even further type of biosensor may employ a polymer substrate, such as a cellulose or nitrocellulose paper, in combination with an optical or electrical detector, for example suitable for a lateral flow test.

The term "dish" as used herein may refer to a vessel or a slide made of glass, ceramic, plastic, cellulose, nitrocellulose or any other material, and can be used as a substrate for microscopic or macroscopic optical detection and selection. Examples include glass slides, microtiter plates, multi-well plates, Petri dishes, watchglasses, etc. The dish may be made of a material that may be modified for example coated with a layer of gold.

The term "microbead" as used herein refers to a particle having a diameter of 1 mm or less. Microbeads may be made of natural or synthetic polymeric materials. Microbeads may be made of a material characterized by having a surface that can be modified, for example they may have a surface that may be conjugated to nanoparticles, such as gold nanoparticles, and/or molecules, such as peptides.

A biosensor refers to a sensor comprising a biological element. Biosensors are practically substitutes of conventional analytical techniques that may be tedious, costly, complex and not appropriate for in situ supervising. A biosensor may be a chemical analytical device unifying a biological element with a transducer. It consolidates a biological element within or in close contact with a transducer which yields a signal proportional to a single analyte that is further conveyed to a detector. In some embodiments, the signal output from the binding of the analyte may be visualized by microscopy. In some embodiments, the signal output from the binding of the analyte may be visualized by an optical detector.

A biosensor embraces three fundamental components that are a bioreceptor (the biological element), a transducer and an electronic circuit. The bioreceptor or biological element is a biomolecule that is embedded with the transducer, like an enzyme, DNA, protein, whole cell, antibodies etc. In the present application, the bioreceptor may be the JUNO protein. In some embodiments of the present disclosure, the biosensor comprises more than one type of bioreceptors, for example a type of bioreceptor may be a JUNO protein or a fragment thereof, and another type of bioreceptor may be selected from a group consisting of ZP1, ZP2, ZP3, and an anti-IZUMO antibody.

Detectors encompassed by the methods of the present disclosure are optical detectors, such as a surface plasmon resonance detector, electrochemical detectors, and measurement circuits. Electronic circuit comprises a signal processing biosensor that converts an electrical signal into a processable signal. In some embodiments, the detector may be a microscope.

Biosensors based on surface plasmon resonance (SPR) effects exploit the shift in SPR surface reflection angle that occurs with perturbations, e.g., binding events, at the SPR interface. Finally, biosensors may also utilize changes in optical properties at a biosensor surface.

Electrochemical biosensors are normally based on enzymatic catalysis of a reaction that produces or consumes electrons (redox enzymes). The sensor substrate usually contains three electrodes; a reference electrode, a working electrode and a counter electrode. The target analyte is involved in the reaction that takes place on the active electrode surface, and the reaction may cause either electron transfer across the double layer (producing a current) or can contribute to the double layer potential (producing a voltage). Either the current can be measured, wherein the rate of flow of electrons is proportional to the analyte concentration at a fixed potential or the potential can be measured at zero current, which gives a logarithmic response. Further, the label-free and direct electrical detection of small peptides and proteins is possible by their intrinsic charges using biofunctionalized ion-sensitive field-effect transistors.

Potentiometric biosensors, in which potential is produced at zero current, gives a logarithmic response with a high dynamic range. Such biosensors are often made by screen printing the electrode patterns on a plastic substrate, coated with a conducting polymer and then some protein (enzyme or antibody) is attached. They have only two electrodes and are extremely sensitive and robust. They enable the detection of analytes at levels previously only achievable by HPLC and LC/MS and without rigorous sample preparation. All biosensors usually involve minimal sample preparation as the biological sensing component is highly selective for the analyte concerned. The signal is produced by electrochemical and physical changes in the conducting polymer layer due to changes occurring at the surface of the sensor. Such changes can be attributed to ionic strength, pH, hydration and redox reactions. Field effect transistors (FET), in which the gate region has been modified with an enzyme or antibody, can also detect very low concentrations of various analytes as the binding of the analyte to the gate region of the FET cause a change in the drain-source current.

Biosensors have a number of potential advantages over conventional binding assay. One important advantage is the ability to manufacture small-scale, but highly reproducible, biosensor units using microchip manufacturing methods.

There are many potential applications of biosensors of various types. The main requirements for a biosensor approach to be valuable in terms of research and commercial applications are the identification of a target molecule, availability of a suitable biological recognition element, and the potential for disposable portable detection biosensors to be preferred to sensitive laboratory-based techniques in some situations.

In one embodiment, the biosensor according to the present disclosure further comprises Zona pellucida 1 (ZP1), Zona pellucida 2 (ZP2), Zona pellucida 3 (ZP3) and/or an anti-IZUMO antibody or fragments thereof, wherein the ZP1, ZP2, ZP3, and/or the anti-IZUMO antibody or fragments thereof are immobilized on the substrate.

In one embodiment, the biosensor according to the present disclosure comprises the proteins JUNO and ZP3, wherein said proteins are immobilized on the substrate.

In one embodiment, the biosensor according to the present disclosure comprises the proteins JUNO and ZP2, wherein said proteins are immobilized on the substrate.

In one embodiment, the biosensor according to the present disclosure comprises the proteins JUNO and ZP1, wherein said proteins are immobilized on the substrate.

In one embodiment, the biosensor according to the present disclosure comprises the proteins JUNO and an anti-IZUMO antibody, wherein said proteins are immobilized on the substrate.

In one embodiment, the biosensor according to the present disclosure comprises the proteins JUNO, ZP2 and ZP3, wherein said proteins are immobilized on the substrate.

Presence of JUNO in combination with one or more of ZP1, ZP2, ZP3 and an anti-IZUMO antibody may improve the specificity of the biosensor and may allow a more precise determination of the sperm function of the analysed semen sample, and/or of the analysed sperm sample. For example, presence of JUNO in combination with one or more of ZP1, ZP2, ZP3 and an anti-IZUMO antibody may allow a more precise determination of the capability of the sperm to bind the zona pellucida proteins, undergo acrosomal reaction and bind an oocyte.

In one embodiment, the proteins JUNO, ZP1, ZP2 and ZP3 which may be immobilized on the substrate are mammalian proteins. For example, the proteins JUNO, ZP1, ZP2 and ZP3 may be human proteins or fragments thereof. For example, the proteins JUNO, ZP1, ZP2 and ZP3 may be equine proteins or fragments thereof. For example, the proteins JUNO, ZP1, ZP2 and ZP3 may be canine proteins or fragments thereof. For example, the proteins JUNO, ZP1, ZP2 and ZP3 may be bovine proteins or fragments thereof.

In a further embodiment, the biosensor according to the present disclosure comprises the JUNO protein comprising or consisting of a polypeptide having at least 95% sequence identity, such as at least 96% sequence identity, such as at least 97% sequence identity, such as at least 98% sequence identity, such as at least 99% sequence identity entity, such as about 100% sequence identity to SEQ ID NO: 1 or an orthologue thereof, or a fragment of said protein.

In one embodiment the biosensor according to the present disclosure is provided, wherein the ZP1 comprises or consists of a polypeptide having at least 95% sequence identity, such as at least 96% sequence identity, such as at least 97% sequence identity, such as at least 98% sequence identity, such as at least 99% sequence identity entity, such as about 100% sequence identity to SEQ ID NO: 2 or an orthologue thereof, or a fragment of said protein.

In a further embodiment the biosensor according to the present disclosure is provided, wherein the ZP2 comprises or consists of a polypeptide having at least 95% sequence identity, such as at least 96% sequence identity, such as at least 97% sequence identity, such as at least 98% sequence identity, such as at least 99% sequence identity entity, such as about 100% sequence identity to SEQ ID NO: 3 or an orthologue thereof, or a fragment of said protein.

In a further embodiment the biosensor according to the present disclosure is provided, wherein the ZP3 comprises or consists of a polypeptide having at least 95% sequence identity, such as at least 96% sequence identity, such as at least 97% sequence identity, such as at least 98% sequence identity, such as at least 99% sequence identity entity, such as about 100% sequence identity to SEQ ID NO: 4 or an orthologue thereof, or a fragment of said protein.

In some embodiments, at least one of the JUNO protein, ZP1, ZP2, ZP3, and anti-IZUMO antibody is conjugated to an additional moiety. For example, said additional moiety may be a peptide or a label. For example, at least one of the JUNO protein, ZP1, ZP2, ZP3, and anti-IZUMO antibody is conjugated to a polyhistidine-tag.

In some embodiments, the biosensor according to the present disclosure is provided, wherein the substrate is microbeads, a dish, a chip or an electrode.

In one embodiment, the substrate is polymeric microbeads. For example, the substrate may be agarose, cellulose, nitrocellulose or latex microbeads. In some embodiments, the microbeads are configured such that it can be coupled to a microscope, an optical transducer or a measurement circuit.

In one embodiment, the substrate is a dish, such as a plastic dish, a ceramic dish or a glass dish. In a further embodiment, said dish is configured such that it can be coupled to a microscope or an optical transducer.

In some embodiments, the chip is a glass chip.

The term "glass" as used herein is equivalent to quartz or silica, comprising silicon and oxygen atoms in a continuous framework with an overall chemical formula of $SiO_2$.

In particular embodiments, the electrode is a carbon, gold or platinum electrode. In one embodiment, the electrode is a screen printed electrode.

In some embodiments, the substrate has a modified surface. In one embodiment, at least one surface of the substrate is coated with a layer of gold. In some embodiments, at least one surface of the substrate is modified with nanoparticles selected from the group consisting of gold, silver, copper oxide, graphene, iron oxide and combinations thereof.

In particular embodiments, the biosensor according to the present disclosure is configured such that the substrate can be coupled to a microscope, an electrochemical workstation, a surface plasmon resonance detector, a measurement circuit or an optical transducer.

In one embodiment, the substrate is an electrode and configured such that it can be coupled to an electrochemical workstation or a measurement circuit.

In one embodiment, the substrate is a chip and is configured such that it can be coupled to a surface plasmon resonance detector.

Immobilization of Proteins

The present disclosure is directed to a biosensor For detection and quantification of sperm function, said biosensor comprising a substrate and the protein JUNO, or a fragment thereof, immobilized on the substrate.

Immobilization of the biological element, such as the protein of interest on the surface of the sensor (be it metal, polymer or glass) is a necessary and critical step in the design of biosensors. Different immobilization techniques exist depending on the substrate employed, these techniques are known to the person skilled in the art.

In some embodiments the biosensor according to the present disclosure is provided, wherein at least one of the JUNO protein, ZP1, ZP2, ZP3, and anti-IZUMO antibody is conjugated to an additional moiety. In some embodiments, the additional moiety is a peptide. In one embodiment, the additional moiety is a label.

In some embodiments, the additional moiety is a peptide, for example a polyhistidine tag (His-tag).

In some embodiments, the additional moiety is a label, also referred to as a fluorescent tag or a probe.

The polyhistidine-tag can be successfully used for the immobilization of proteins on a surface such as on a metal surface, for example a gold-, nickel- or cobalt-coated microtiter plate or on a protein array.

In some embodiments the biosensor according to the present disclosure is provided, wherein the JUNO protein, ZP1, ZP2, ZP3 and/or the anti-IZUMO antibody is immobilized on the substrate.

In some embodiments the biosensor according to the present disclosure is provided, wherein the JUNO protein, ZP1, ZP2, ZP3 and/or the anti-IZUMO antibody is immobilized on the substrate via a nanoparticle, for example via a gold nanoparticle. The presence of a nanoparticle between the substrate and the protein is advantageous as it prevents unfolding of the protein and helps the protein to stay in the correct conformation.

Methods

It is an aspect of the disclosure to provide a method for manufacturing a biosensor comprising a JUNO protein, such as a biosensor disclosed herein, the method comprising:
 a. providing a substrate,
 b. providing the JUNO protein,
 c. immobilizing the JUNO protein on the substrate,
 thereby manufacturing a biosensor comprising the JUNO protein.

In some embodiments, the method for manufacturing a biosensor further comprises immobilizing on the substrate one or more of ZP1, ZP2, ZP3 and an anti-IZUMO antibody.

It is a further aspect of the disclosure to provide a method of selecting sperm, said method comprising:
 a. Providing a semen sample from a subject,
 b. Contacting the semen sample with the biosensor according to the present disclosure,
 c. Visualizing a sperm bound to the biosensor by microscopy, and
 d. Selecting sperm bound to the biosensor.

It is a further aspect of the disclosure to provide a method of selecting sperm, said method comprising:
 a. Providing a sperm sample from a subject,
 b. Contacting the sperm sample with the biosensor according to the present disclosure,
 c. Visualizing a sperm bound to the biosensor by microscopy, and
 d. Selecting sperm bound to the biosensor.

In one embodiment according to the method of the present disclosure, the semen sample comprises, or is suspected of comprising, one or more sperm cells.

Home Device

It is also an aspect of the disclosure to provide a hand-held device for detection and/or quantification of sperm function, the device comprising:

a. An inlet for a sample;
b. A biosensor comprising a JUNO protein or a fragment thereof, wherein the JUNO protein is immobilized on the biosensor, and wherein the inlet is configured to place the sample in contact with the sensor;
c. A detector configured to receive a signal from the sensor and transform it into a format readable by a user;
d. Optionally, means for separating cellular components from the sample.

In particular embodiments, the hand-held device according to the present disclosure comprises the biosensor as defined in any one of the embodiments of the present disclosure.

Subjects

It is an aspect of the disclosure to provide a method according to the present disclosure, wherein the subject is a human subject. In particular embodiments, the human subject is a child or an adult.

In further embodiments of the method according to the present disclosure, the subject is a mammal. In further embodiments of the method according to the present disclosure, the subject is a horse, cow, buffalo, sheep, pig, goat, cat or dog.

In some embodiments of the present disclosure, the subject is a horse, and the biosensor comprises a JUNO protein or a fragment thereof immobilized on the substrate, wherein said JUNO protein has a sequence having at least 95% sequence identity to an equine JUNO protein of SEQ ID NO: 6, such as at least 96% sequence identity, such as at least 97% sequence identity, such as at least 98% sequence identity, such as at least 98% sequence identity, such as at least 99% sequence identity, such as about 100% sequence identity to said an equine JUNO protein of SEQ ID NO: 6.

In some embodiments of the present disclosure, the subject is a dog, and the biosensor comprises a JUNO protein or a fragment thereof immobilized on the substrate, wherein said JUNO protein is a canine JUNO protein.

In some embodiments of the present disclosure, the subject is a cow, and the biosensor comprises a JUNO protein or a fragment thereof immobilized on the substrate, wherein said JUNO protein is a bovine JUNO protein.

Sample

In particular embodiments of the methods according to the present disclosure, the sample is a semen sample, optionally wherein the sample has been treated prior to analysis.

In particular embodiments of the methods according to the present disclosure, the sample is a sperm sample, optionally wherein the sample has been treated prior to analysis.

In one embodiment according to the method of the present disclosure, the semen sample and/or the sperm sample comprises, or is suspected of comprising, one or more sperm cells.

In some embodiments, the semen sample is treated prior to analysis and said treatment comprises liquefaction of the sperm.

Semen sample may herein be used interchangeably with sperm sample and seminal fluid. A semen sample and/or a sperm sample is defined herein as a sample of seminal fluid that may contain spermatozoa. The semen sample may further, in specific embodiments of the present disclosure, be treated, such as diluted, by the use of solvents, mediums, buffers and/or fluids suitable for the treatment, such as dilution, of semen/sperm samples.

Semen is secreted by the gonads (sexual glands) and other sexual organs of male or hermaphroditic animals and can fertilize female ova. In humans, seminal fluid contains several components besides spermatozoa: proteolytic and other enzymes as well as fructose are elements of seminal fluid, which promote the survival of spermatozoa, and provide a medium through which they can move or "swim". Semen is produced and originates from the seminal vesicle, which is located in the pelvis.

The term "sperm" has used herein refers to the male reproductive cell and is synonymous of "sperm cell". A uniflagellar sperm cell that is motile is referred to as a spermatozoon, whereas a non-motile sperm cell is referred to as a spermatium. Within the present disclosure, the terms "sperm" and "spermatozoa" are used interchangeably.

Detection Technologies

In some embodiments of the methods according to the present disclosure, the sperm function is detected using surface plasmon resonance (SPR). In particular embodiments, the surface plasmon resonance readout is used to determine the concentration of one or more of the thyroid hormones.

Surface plasmon resonance is the resonant oscillation of conduction electrons at the interface between negative and positive permittivity material stimulated by incident light. SPR is the basis of many standard tools for measuring adsorption of material onto planar metal (such as gold or silver) surfaces or onto the surface of metal nanoparticles. It is the fundamental principle behind many color-based biosensor applications, different sensors and diatom photosynthesis. SPR may be used to detect biomolecular binding interactions. In SPR, one molecular partner such as a protein is immobilized on a metallic film. Light excites surface plasmons in the metal; when the binding partner binds to the immobilized molecule, this causes a detectable change in the surface plasmon signal.

In some embodiments of the methods according to the present disclosure, the sperm function is detected or quantified by electrochemical transduction.

Electrochemical biosensors, also referred to as biosensors utilizing electrochemical transduction provide an attractive means to analyze the content of a biological sample due to the direct conversion of a biological event to an electronic signal. The most common techniques in electrochemical biosensing comprise cyclic voltammetry, chronoamperometry, chronopotentiometry, impedance spectroscopy, and field-effect transistor based methods along with nanowire or magnetic nanoparticle-based biosensing. Additional measurement techniques useful in combination with electrochemical detection may further comprise the electrochemical versions of surface plasmon resonance, optical waveguide lightmode spectroscopy, ellipsometry, quartz crystal microbalance, and scanning probe microscopy.

Male Infertility

Male infertility refers to a male's inability to cause pregnancy in a fertile female. In humans it accounts for 40-50% of infertility. It affects approximately 7% of all men. Male infertility is commonly due to deficiencies in the semen, and semen quality is used as a surrogate measure of male fecundity.

Male infertility is defined as the inability of a male individual to cause pregnancy in a fertile female individual. A cause of male infertility may be the production of non-functional sperm.

A diagnosis of male infertility may be based on a battery of functional tests, for example on any one of the sperm functions tests disclosed herein. The tests may be evaluated according to guidelines known to the person of skill in the art, for example as described in the WHO laboratory manual for the Examination and processing of human semen, WHO, 5th Edition, 2010, ISBN 978 92 4 154778 9 (see in particular Chapter 4).

Sequences

SEQ ID NO: 1: JUNO_HUMAN Sperm-egg fusion protein Juno
MACVWVPLLLELWTVMPTWAGDELLNICMNAKHHKRVPSPEDKLYEECIP
WKDNACCTLTTSWEAHLDVSPLYNFSLFHCGLLMPGCRKHFIQAICFYEC
SPNLGPWIQPVGSLGWEVAPSGQGERVVNVPLCQEDCEEVWVEDCRMSYT
CKSNWRGGWDWSQGKNRCPKGAQCLPFSHYFPTPADLCEKTWSNSFKASP
ERRNSGRCLQKWFEPAQGNPNVAVARLFASSAPSWELSYTIMVCSLFLPF
LS SEQ ID NO: 2: ZP1_HUMAN Zona pellucida sperm-binding protein 1
MAGGSATTWGYPVALLLLVATLGLGRWLQPDPGLPGLRHSYDCGIKGMQL
LVFPRPGQTLRFKVVDEFGNRFDVNNCSICYHWVTSRPQEPAVFSADYRG
CHVLEKDGRFHLRVFMEAVLPNGRVDVAQDATLICPKPDPSRTLDSQLAP
PAMFSVSTPQTLSFLPTSGHTSQGSGHAFPSPLDPGHSSVHPTPALPSPG
PGPTLATLAQPHWGTLEHWDVNKRDYIGTHLSQEQCQVASGHLPCIVRRT
SKEACQQAGCCYDNTREVPCYYGNTATVQCFRDGYFVLVVSQEMALTHRI
TLANIHLAYAPTSCSPTQHTEAFVVFYFPLTHCGTTMQVAGDQLIYENWL
VSGIHIQKGPQGSITRDSTFQLHVRCVFNASDFLPIQASIFPPPSPAPMT
QPGPLRLELRIAKDETFSSYYGEDDYPIVRLLREPVHVEVRLLQRTDPNL
VLLLHQCWGAPSANPFQQPQWPILSDGCPFKGDSYRTQMVALDGATPFQS
HYQRFTVATFALLDSGSQRALRGLVYLFCSTSACHTSGLETCSTACSTGT
TRQRRSSGHRNDTARPQDIVSSPGPVGFEDSYGQEPTLGPTDSNGNSSLR
PLLWAVLLLPAVALVLGFGVFVGLSQTWAQKLWESNRQ SEQ ID NO: 3: ZP2_HUMAN Zona pellucida sperm-binding protein 2
MACRQRGGSWSPSGWFNAGWSTYRSISLFFALVTSGNSIDVSQLVNPAFP
GTVTCDEREITVEFPSSPGTKKWHASVVDPLGLDMPNCTYILDPEKLTLR
ATYDNCTRRVHGGHQMTIRVMNNSAALRHGAVMYQFFCPAMQVEETQGLS
ASTICQKDFMSFSLPRVFSGLADDSKGTKVQMGWSIEVGDGARAKTLTLP
EAMKEGFSLLIDNHRMTFHVPFNATGVTHYVQGNSHLYMVSLKLTFISPG
QKVIFSSQAICAPDPVTCNATHMTLTIPEFPGKLKSVSFENQNIDVSQLH
DNGIDLEATNGMKLHFSKTLLKTKLSEKCLLHQFYLASLKLTFLLRPETV
SMVIYPECLCESPVSIVTGELCTQDGFMDVEVYSYQTQPALDLGTLRVGN
SSCQPVFEAQSQGLVRFHIPLNGCGTRYKFEDDKVVYENEIHALVVTDFP
PSKISRDSEFRMTVKCSYSRNDMLLNINVESLTPPVASVKLGPFTLILQS
YPDNSYQQPYGENEYPLVRFLRQPIYMEVRVLNRDDPNIKLVLDDCWATS
TMDPDSFPQWNVVVDGCAYDLDNYQTTFHPVGSSVTHPDHYQRFDMKAFA
FVSEAHVLSSLVYFHCSALICNRLSPDSPLCSVTCPVSSRHRRATGATEA
EKMTVSLPGPILLLSDDSSFRGVGSSDLKASGSSGEKSRSETGEEVGSRG
AMDTKGHKTAGDVGSKAVAAVAAFAGVVATLGFIYYLYEKRTVSNH SEQ ID NO: 4: ZP3_HUMAN Zona pellucida sperm-binding protein 3
MELSYRLFICLLLWGSTELCYPQPLWLLQGGASHPETSVQPVLVECQEAT
LMVMVSKDLFGTGKLIRAADLTLGPEACEPLVSMDTEDVVRFEVGLHECG
NSMQVTDDALVYSTFLLHDPRPVGNLSIVRTNRAEIPIECRYPRQGNVSS
QAILPTWLPFRTTVFSEEKLTFSLRLMEENWNAEKRSPTFHLGDAAHLQA
EIHTGSHVPLRLFVDHCVATPTPDQNASPYHTIVDFHGCLVDGLTDASSA
FKVPRPGPDTLQFTVDVFHFANDSRNMIYITCHLKVTLAEQDPDELNKAC
SFSKPSNSWFPVEGSADICQCCNKGDCGTPSHSRRQPHVMSQWSRSASRN
RRHVTEEADVTVGPLIFLDRRGDHEVEQWALPSDTSVVLLGVGLAVVVSL
TLTAVILVLTRRCRTASHPVSASE SEQ ID NO: 5: IZUMO1_HUMAN Izumo sperm-egg fusion protein 1
MGPHFTLLCAALAGCLLPAEGCVICDPSVVLALKSLEKDYLPGHLDAKHH
KAMMERVENAVKDFQELSLNEDAYMGVVDEATLQKGSWSLLKDLKRITDS
DVKGDLFVKELFWMLHLQKETFATYVARFQKEAYCPNKCGVMLQTLIWCK
NCKKEVHACRKSYDCGERNVEVPQMEDMILDCELNWHQASEGLTDYSFYR -continued Sequences VWGNNTETLVSKGKEATLTKPMVGPEDAGSYRCELGSVNSSPATIINFHV
TVLPKMIKEEKPSPNIVTPGEATTESSISLQPLQPEKMLASRLLGLLICG
SLALITGLTFAIFRRRKVIDFIKSSLFGLGSGAAEQTQVPKEKATDSRQQ

EXAMPLES

Example 1. Electrochemical Biosensor for Sperm Binding Employing Cyclic Voltammetry The biosensors were fabricated on a screen-printed gold electrode. Briefly, 10 μL of 2 mg/mL cysteamine hydrochloride was added on the gold electrode and allowed to dry in dark at room temperature. The electrode was washed with deionized water followed by modification with 10 μL of citrate-capped gold nanoparticles. After drying and washing with deionized water, 10 μL of 50 mM nitrilotriacetic acid was added and incubated overnight at room temperature. This was followed by blocking with 1% bovine serum albumin in 0.01 M phosphate buffer saline at pH 7.4. 10 μL of 10 mM nickel sulfate was added and incubated at room temperature for 2 hours. After washing the electrode with 0.01 M phosphate buffer saline at pH 7.4, 0.5 μg of JUNO or ZP3 containing a polyhistidine tag were immobilized on the biosensor.

Semen samples were allowed to liquefy following standard procedures and diluted to different dilutions in a semen preparation medium (#1070/1069, Origio A/S Denmark, https://origio.marketport.net/MarketingZone/MZDirect/Source/510e96f4-075b-4684-9a99-d472c1e3d31b). The biosensor was connected to an electrochemical station, diluted semen sample was added on the biosensor, and the cyclic voltammetric response of the interaction between the immobilized proteins and the sperms present in the semen sample was recorded.

The results are shown in FIG. 1-FIG. 3F, wherein FIG. 1 shows the cyclic voltammetric response of a) Electrode-gold nanoparticles-BSAblocking after addition of buffer only (solid line) and after addition of semen sample diluted $1.67 \times 10^{-2}$X in buffer (dotted line) b) Electrode-gold nanoparticles-JUNO-BSAblocking (dash dot dot line) and c) Electrode-gold nanoparticles-ZP3-BSAblocking response (dashed line) after addition of semen sample diluted $1.67 \times 10^{-2}$X in buffer, with the dilution factor given by the initial volume/final volume.

FIG. 2A to FIG. 2F show cyclic voltammetric response of Electrode-gold nanoparticles-ZP3-BSAblocking after addition of three different dilutions ($1.56 \times 10^{-5}$X (dotted line), $1.67 \times 10^{-2}$X (dash dot dot line) and $2.5 \times 10^{-2}$X (dashed line)) of 6 different semen samples (FIG. 2A-FIG. 2F), while solid line shows electrode response with buffer only (no semen sample).

FIG. 3A to FIG. 3F shows cyclic voltammetric response of Electrode-gold nanoparticles-JUNO-BSAblocking after addition of three different dilutions ($1.56 \times 10^{-5}$X (dotted line), $1.67 \times 10^{-2}$X (dash dot dot line) and $2.5 \times 10^{-2}$X (dashed line)) of semen samples S1, S2, S3, S4, S5 and S6 (FIG. 3A-FIG. 3F, respectively), while solid line shows electrode response with buffer only (no semen sample).

Conclusion:

As shown in FIG. 1, sperms do not bind to a biosensor without JUNO or ZP3 immobilized. In presence of JUNO or ZP3, the spermatozoa interact with the biosensor as evident from the distinct reduction and/or oxidation peaks in the cyclic voltammetric curves. Further, the binding is quantifiable using cyclic voltammetry. For both, ZP3-spermatozoa and JUNO-spermatozoa interactions, the reduction and oxidation peaks shift in a trend consistent with the number of spermatozoa available for the binding with ZP3 and JUNO, as shown in FIG. 2A-FIG. 2F and FIG. 3A-FIG. 3F, respectively. Further, as the signal remains unchanged between null and non-zero sperm concentrations for negative control, i.e. upon absence of the binding proteins (FIG. 1), the probed interactions are protein-specific.

Example 2. Electrochemical Biosensor for Sperm Binding Analysed Employing Electro-Impedance Spectroscopy Screen printed gold electrodes are functionalized via 10 μl of 2 mg/ml Cysteamine hydrochloride (CyHCl) and incubated in dark for 2-4 h at room temperature. After washing the electrode with deionized water, 5 μl of Asn-AuNPs are dispensed onto the functionalized electrode. The electrode is incubated for 5 h at room temperature and then washed with deionized water. Further 5 μl of 160 μg/ml of JUNO and 160 μg/ml ZP3 in 5 μl PB (10 mM, pH 7.4) is added and incubated overnight at 4° C. Finally the electrode is blocked with 10 μl of 1% BSA in PBS for 5 h at 4° C.

The modified electrode is connected to an electrochemical workstation. 5-50 uL of pre-treated semen sample is added on to the working electrode, or the electrode is immersed in the sample vial. The sperm cells are allowed to bind to the modified electrode for 1-10 minutes, followed by washing with deionized water. The binding is analysed via electro-impedance spectroscopy in presence of suitable concentrations of a redox mediator.

Similar experiments are performed using JUNO only, ZP2 and combination of ZP2, ZP3, JUNO.

For this and all the following examples, the semen sample is pre-treated (liquefied) prior to analysis according to the following procedure:

The semen sample collected in the laboratory or clinic is allowed to liquefy at room temperature or in an incubator at 37° C. for 15-60 minutes. This may be assisted by gentle rotation or stirring to prevent heterogeneously liquefied semen sample.

This liquefied semen sample may undergo washing, reconstitution or dilution with a suitable semen preparation medium.

Conclusion:

A sensor comprising screen printed gold electrodes functionalized and modified with JUNO, or a combination of JUNO and any one of ZP2 and ZP3 or combinations thereof, can be used to detect and quantify sperm function via an electrochemical workstation.

Example 3. Electrochemical Biosensor for Acrosomal Reaction

Screen printed gold electrodes are functionalized via 10 μl of 2 mg/ml Cysteamine hydrochloride (CyHCl) and incubated in dark for 2-4 h at room temperature. After washing the electrode with deionized water, 5 μl of Asn-AuNPs are dispensed onto the functionalized electrode. The electrode is then incubated for 5 h at room temperature and then washed with deionized water. Further 5 μl of 160 μg/ml of JUNO and 160 μg/ml ZP3 in 5 μl PB (10 mM, pH 7.4) is added and incubated overnight at 4° C. Finally the electrode is blocked with 10 μl of 1% BSA in PBS for 5 h at 4° C.

The modified electrode is connected to an electrochemical workstation. 5-50 uL of pre-treated semen sample is added on to the working electrode, or the electrode is immersed in the sample vial. The sperm cells are allowed to bind to the modified electrode while the binding is analysed electrochemically via electro-impedance spectroscopy or amperometry.

Similar experiments are performed using ZP2 and combination of JUNO, ZP3, ZP2.

Conclusion:

A sensor comprising screen printed gold electrodes functionalized and modified with JUNO, or a combination of JUNO and any one of ZP2 and ZP3 or combinations thereof, can be used to detect and quantify sperm function via an electrochemical workstation.

Example 4. Detection/Quantification of Sperm Function Via Surface Plasmon Resonance (SPR)

SPR chips are chemically functionalized and modified with any one of ZP2, ZP3 and JUNO, or combinations thereof. The chips are then washed with deionized water, and the uncoated area is blocked with bovine serum albumin (BSA). The chips are used in conjunction with an SPR detector. A flow of a pre-treated semen sample is let over the chip's surface. The interaction between the protein coat and the sperm cells is analyzed as a mass change in terms of binding kinetics and affinity. Sperm function is thereby detected and quantified.

Conclusion:

A sensor comprising SPR chips are chemically functionalized and modified with any one of ZP2, ZP3 and JUNO, or combinations thereof can be used to detect and quantify sperm function via an SPR detector.

Example 5. Detection/Quantification of Sperm Binding Via an Optical Transducer Whole or a part of a glass dish is chemically functionalized and modified first with AuNPs and then with any one of ZP2, ZP3 and JUNO, or combinations thereof. The dish is washed with deionized water, and the uncoated area is blocked with BSA. A drop of pre-treated semen sample is added on to the coated area, and visualized for binding under an optical transducer such as a bright field or dark field microscope. Sperm function is thereby detected and quantified.

Conclusion:

A sensor comprising any one of ZP2 and ZP3, or combinations thereof conjugated with AuNPs or AuNPs modified glass or plastic dish can be used to detect and quantify sperm function via an optical transducer.

Example 6. Detection/Quantification of Acrosomal Reaction Via an Optical Transducer The pre-treated semen sample is incubated with any one of ZP2 and ZP3, or combinations thereof, which have previously been conjugated with AuNPs. The sperms are allowed to interact with the proteins for 5-60 minutes, followed by washing via centrifugation. The sperms are then stained for acrosomal reaction with *Pisum sativum* agglutinin (PSA) labelled with fluorescein isothiocyanate (FITC) (PSA-FITC), and then visualized under an optical transducer such as a fluorescence microscope or a flow cytometer (see section 4.4.1 in http://apps.who.int/iris/bitstream/handle/10665/44261/9789241547789_eng.pdf;jsessio nid=2EF9F9030760BB60B84C83708999AF64?sequence=1). Sperm function is thereby detected and quantified.

Alternatively, the pre-treated semen sample is incubated with any one of ZP2 and ZP3, or combinations thereof which have previously been conjugated with AuNP modified glass or plastic dish, for 5-60 minutes. The sperms are removed from the surface and then stained for acrosomal reaction with PSA-FITC, and then visualized under an optical transducer such as a fluorescence microscope or a flow cytometer. Sperm function is thereby detected and quantified.

Alternatively, the pre-treated semen sample is incubated with any one of ZP2 and ZP3, or combinations thereof, which have previously been conjugated with AuNP modified glass or plastic dish, for 5-60 minutes. The sperms are then labelled with anti-CD46 antibodies in situ or after removal from the substrate to detect sperms that have undergone acrosomal reaction. The detection is performed via an optical transducer such as a fluorescence microscope or a flow cytometer. Sperm function is thereby detected and quantified.

Conclusion:

A sensor comprising any one of ZP2, ZP3 and JUNO, or combinations thereof conjugated with AuNPs or AuNPs modified glass or plastic dish can be used to detected and quantify sperm function via an optical transducer.

Exemplary Embodiments

Embodiment 1: A biosensor for detection and/or quantification of sperm binding function, the biosensor comprising a substrate and a JUNO protein or a fragment thereof, wherein the JUNO protein or fragment thereof is immobilized on the substrate, and wherein the biosensor is configured for determining binding of a sperm cell to a protein immobilized on the substrate.

Embodiment 2: The biosensor according to any one of the preceding Embodiments, further comprising Zona pellucida 1 (ZP1), Zona pellucida 2 (ZP2), Zona pellucida 3 (ZP3) and/or an anti-IZUMO antibody or fragments thereof, wherein the ZP1, ZP2, ZP3, and/or the anti-IZUMO antibody or fragments thereof are immobilized on the substrate.

Embodiment 3: The biosensor according to any one of the preceding Embodiments, wherein the proteins JUNO, ZP1, ZP2 and ZP3 are mammalian proteins.

The biosensor according to any one of the preceding Embodiments, wherein the proteins JUNO, ZP1, ZP2 and ZP3 are human, equine, canine or bovine proteins.

Embodiment 4: The biosensor according to any one of the preceding Embodiments, wherein the JUNO protein comprises or consists of a polypeptide having at least 95% sequence identity, such as at least 96% sequence identity, such as at least 97% sequence identity, such as at least 98% sequence identity, such as at least 99% sequence identity entity, such as about 100% sequence identity to a protein of SEQ ID NO: 1 or an orthologue thereof, or a fragment of said protein.

Embodiment 5: The biosensor according to any one of the preceding Embodiments, wherein the ZP1 comprises or consists of a polypeptide having at least 95% sequence identity, such as at least 96% sequence identity, such as at least 97% sequence identity, such as at least 98% sequence identity, such as at least 99% sequence identity entity, such as about 100% sequence identity to SEQ ID NO: 2 or an orthologue thereof, or a fragment of said protein.

Embodiment 6: The biosensor according to any one of the preceding Embodiments, wherein the ZP2 comprises or consists of a polypeptide having at least 95% sequence identity, such as at least 96% sequence identity, such as at least 97% sequence identity, such as at least 98% sequence identity, such as at least 99% sequence identity entity, such as about 100% sequence identity to SEQ ID NO: 3 or an orthologue thereof, or a fragment of said protein.

Embodiment 7: The biosensor according to any one of the preceding Embodiments, wherein the ZP3 comprises or consists of a polypeptide having at least 95% sequence identity, such as at least 96% sequence identity, such as at least 97% sequence identity, such as at least 98% sequence identity, such as at least 99% sequence identity entity, such as about 100% sequence identity to SEQ ID NO: 4 or an orthologue thereof, or a fragment of said protein.

Embodiment 8: The biosensor according to any one of the preceding Embodiments, wherein at least one of the JUNO protein, ZP1, ZP2, ZP3, and anti-IZUMO antibody is conjugated to an additional moiety.

Embodiment 9: The biosensor according to any one of the preceding Embodiments, wherein said additional moiety is a peptide.

Embodiment 10: The biosensor according to any one of the preceding Embodiments, wherein said additional moiety is a label.

Embodiment 11: The biosensor according to any one of the preceding Embodiments, wherein the sperm binding function is determined from the binding of at least a portion of the sperm cell to a protein immobilized on the substrate, wherein said protein is selected from the groups consisting of JUNO protein, ZP1, ZP2, ZP3 and/or the anti-IZUMO antibody, or fragments thereof.

Embodiment 12: The biosensor according to any one of the preceding Embodiments, wherein at least a portion of the sperm cell comprises an IZUMO1 surface antigen.

Embodiment 13: The biosensor according to any one of the preceding Embodiments, wherein the substrate is a microbead, a dish, a chip or an electrode.

Embodiment 14: The biosensor according to any one of Embodiments 1-12, wherein the substrate is an electrode.

Embodiment 15: The biosensor according to any one of the preceding Embodiments, wherein the substrate is a polymeric microbead.

Embodiment 16: The biosensor according to any one of the preceding Embodiments, wherein the substrate is agarose, cellulose, nitrocellulose or latex microbeads.

Embodiment 17: The biosensor according to any one of the preceding Embodiments, wherein the substrate is a dish, such as a plastic dish, a ceramic dish or a glass dish.

Embodiment 18: The biosensor according to any one of the preceding Embodiments, wherein the substrate is a dish and wherein said dish is configured such that it can be coupled to a microscope or an optical transducer.

Embodiment 19: The biosensor according to any one of the preceding Embodiments, wherein the substrate is microbeads, wherein said microbeads are configured such that they can be coupled to a microscope, an optical transducer or a measurement circuit.

Embodiment 20: The biosensor according to any one of the preceding Embodiments, wherein chip is a glass chip.

Embodiment 21: The biosensor according to any one of the preceding Embodiments, wherein the electrode is a carbon, gold or platinum electrode.

Embodiment 22: The biosensor according to any one of the preceding Embodiments, wherein the electrode is a screen printed electrode.

Embodiment 23: The biosensor according to any one of the preceding Embodiments, wherein the substrate has a modified surface.

Embodiment 24: The biosensor according to any one of the preceding Embodiments, wherein at least a portion of the substrate is coated with a layer of gold.

Embodiment 25: The biosensor according to any one of the preceding Embodiments, wherein at least a portion of the substrate is modified with nanoparticles selected from the group consisting of gold, silver, copper oxide, graphene, iron oxide and combinations thereof.

Embodiment 26: The biosensor according to any one of the preceding Embodiments, wherein the JUNO protein, ZP1, ZP2, ZP3 and/or the anti-IZUMO antibody is immobilized on the substrate.

Embodiment 27: The biosensor according to any one of the preceding Embodiments, configured such that the substrate can be coupled to a microscope, an electrochemical workstation, a surface plasmon resonance detector, a measurement circuit or an optical transducer.

Embodiment 28: The biosensor according to any one of the preceding Embodiments, wherein the substrate is a dish and wherein said dish is configured such that it can be coupled to a microscope or an optical transducer.

Embodiment 29: The biosensor according to any one of the preceding Embodiments, wherein the substrate is an electrode and wherein said electrode is configured such that it can be coupled to an electrochemical workstation or a measurement circuit.

Embodiment 30: The biosensor according to any one of the preceding Embodiments, wherein the substrate is a chip and wherein said chip is configured such that it can be coupled to a surface plasmon resonance detector.

Embodiment 31: The biosensor according to any one of the preceding Embodiments, wherein the biosensor is configured for detection and/or quantification of sperm binding function, wherein said sperm is in a semen sample.

Embodiment 32: A method for detecting and/or quantifying sperm binding function, wherein the method comprises the steps of:
 a. Providing a semen sample from a subject, wherein said semen sample comprises one or more sperm cells,
 b. Contacting the semen sample with the biosensor according to any one of the preceding Embodiments,
 c. Determining binding of the sperm cells to a protein immobilized on the substrate,
 a. thereby detecting and/or quantifying the sperm binding function of said sample.

Embodiment 33: A method for diagnosis of male infertility, wherein the method comprises the steps of:
 a. Providing a semen sample from a subject,
 b. Contacting the semen sample with the biosensor according to any one of the preceding Embodiments,
 c. Quantifying the sperm binding function of said sample according to the method of Embodiment 32,
 d. Using the sperm binding function to diagnose if the subject is infertile.

Embodiment 34: The method according to any one of Embodiment 33, wherein the semen sample comprises one or more sperm cells.

Embodiment 35: The method according to any one of Embodiments 32 to 34, wherein the protein immobilized on the substrate is selected from the group consisting of JUNO protein, ZP1, ZP2, ZP3 and/or the anti-IZUMO antibody, or fragments thereof, and wherein said binding is detected by microscopic analysis, electrochemical detection and/or surface plasmon resonance.

Embodiment 36: The method according to any one of Embodiments 32 and 35, wherein the sperm binding function of said sample is quantified by determining the percentage of bound versus unbound sperm cells by microscopic analysis, electrochemical detection and/or surface plasmon resonance.

Embodiment 37: The method according to any one of Embodiments 32 to 36, wherein the sperm binding function of said sample is quantified by determining the acrosomal status of the sperm cells in the semen sample by microscopic analysis, electrochemical detection and/or surface plasmon resonance.

Embodiment 38: The method according to any one of Embodiments 32 to 37, wherein said method further comprises comparing the percentage of bound versus unbound sperm cells and/or the acrosomal status of the sperm cells with respective reference values.

Embodiment 39: The method according to any one of Embodiments 32 to 38, wherein the semen sample is treated prior to step b., and wherein said treatment comprises liquefaction of said sample and optionally capacitation.

Embodiment 40: The method according to any one of Embodiments 32 to 39, wherein the method further comprises a step of adding a fluorophore to the sample prior to quantifying the sperm binding function of said sample.

Embodiment 41: The method according to any one of Embodiments 32 to 40, wherein sperm binding function is determined by the ability of a sperm cell to bind to the immobilized JUNO protein.

Embodiment 42: The method according to any one of Embodiments 32 to 41, wherein said binding of the sperm cell to the immobilized JUNO proteins occurs via an IZUMO1 protein expressed by the sperm cell.

Embodiment 43: The method according to any one of Embodiments 32 to 42, further comprising a step of treating said male infertility.

Embodiment 44: The method according to Embodiments 43, wherein the treatment comprises administration of a medicament in a therapeutically effective amount and/or an artificial reproductive technology (ART).

Embodiment 45: The method according to any one of Embodiments 32 to 44, wherein the subject is a human subject.

Embodiment 46: The method according to any one of Embodiments 32 to 45, wherein the human subject is a child or an adult.

Embodiment 47: The method according to any one of Embodiments 32 to 46, wherein the subject is a mammal, such as a horse, cow, buffalo, sheep, pig, goat, cat or dog.

Embodiment 48: A method of selecting sperm, said method comprising:
 a. Providing a semen sample from a subject, wherein said semen sample comprises one or more sperm cells,
 b. Contacting the semen sample with the biosensor according to any one of the preceding Embodiments,
 c. Visualizing a sperm cell bound to the biosensor by microscopy, and
 d. Selecting at least one sperm cell bound to the biosensor.

Embodiment 49: A method for manufacturing a biosensor comprising a JUNO protein according to Embodiment 1, the method comprising:
 a. Providing a substrate,
 b. providing the JUNO protein, and
 c. immobilizing the JUNO protein on the substrate,
 d. providing means for determining binding of a sperm cell to a protein immobilized on the substrate, a. thereby manufacturing a biosensor comprising the JUNO protein.

Embodiment 50: The method according to Embodiment 49, wherein the substrate is as defined in any one of the preceding Embodiments.

Embodiment 51: The method according to any one of Embodiments 49 to 50, wherein the method further comprises immobilizing on the substrate one or more of ZP1, ZP2, ZP3 and an anti-IZUMO antibody.

Embodiment 52: The method according to any one Embodiments 49 to 51, wherein the proteins JUNO, ZP1, ZP2, ZP3 and the anti-IZUMO antibody are as defined in any one of the preceding Embodiments.

Embodiment 53: A hand-held device for detection and/or quantification of sperm binding function, the device comprising:

a. An inlet for a sample;
b. A biosensor comprising a JUNO protein or a fragment thereof, wherein the JUNO protein is immobilized on the biosensor, wherein the biosensor is configured for determining binding of a sperm cell to a protein immobilized on the substrate, and wherein the inlet is configured to place the sample in contact with the substrate;
c. A detector configured to receive a signal from the substrate and transform it into a format readable by a user; and
d. Optionally, means for separating cellular components from the sample.

Embodiment 54: The hand-held device according to Embodiment 53, wherein the biosensor is as defined in any one of the preceding Embodiments.

The invention claimed is:

1. A biosensor for detection or quantification of sperm binding function, the biosensor comprising
an Izumo sperm-egg fusion 1 receptor (JUNO) protein or a fragment thereof (first fragment) immobilized on a substrate which is a dish, a microbead, or an electrode, and the JUNO protein or the first fragment, when immobilized on the substrate, binds a sperm, wherein at least a portion of the sperm comprises an IZUMO1 surface antigen.

2. The biosensor according to claim 1, wherein the JUNO protein is mammalian.

3. The biosensor according to claim 1, wherein the JUNO protein comprises or consists of a polypeptide having at least 95% sequence identity to a protein of SEQ ID NO: 1 or an orthologue thereof.

4. The biosensor according to claim 1, wherein the JUNO protein or the first fragment is conjugated to an additional moiety selected from a peptide and a label.

5. The biosensor according to claim 1,
wherein said dish is coupled to a microscope or an optical transducer, or
wherein said microbead is coupled to a microscope, an optical transducer, or a measurement circuit, or
wherein said electrode is coupled to an electrochemical workstation or a measurement circuit.

6. The biosensor according to claim 1, wherein at least a portion of the substrate is modified with nanoparticles selected from the group consisting of gold, silver, copper oxide, graphene, iron oxide, and combinations thereof.

7. A method for detecting or quantifying sperm function, wherein the method comprises the steps of:
a) providing a semen sample from a subject, wherein said semen sample comprises one or more sperm cells,
b) binding any sperm cells in the sample that exhibit IZUMO1 as a surface antigen by contacting the semen sample with a biosensor comprising an Izumo sperm-egg fusion 1 receptor (JUNO) protein or a fragment thereof immobilized on a substrate, said substrate is a dish, a microbead, or an electrode, and wherein the JUNO protein or the fragment, when immobilized on the substrate, binds a sperm, wherein at least a portion of the sperm comprises an IZUMO1 surface antigen, and
c) detecting or quantifying any sperm cells bound to the JUNO protein or the fragment thereof that is immobilized on the substrate, thereby detecting or quantifying the sperm function of said sample.

8. A method of using a biosensor comprising an Izumo sperm-egg fusion 1 receptor (JUNO) protein or a fragment thereof immobilized on a substrate, said substrate is a dish, a microbead, or an electrode, and wherein the JUNO protein or the fragment, when immobilized on the substrate, binds a sperm, wherein at least a portion of the sperm comprises an IZUMO1 surface antigen, to diagnose male infertility in a subject, wherein the method comprises the steps of:

a) contacting a semen sample obtained from the subject with the biosensor, and
b) detecting or quantifying any sperm in the semen sample that bind the JUNO protein or the fragment thereof that is immobilized on the substrate to diagnose if the subject is infertile.

9. The method according to claim 8, further comprising a step of treating said male infertility, wherein the treatment comprises administration of a medicament in a therapeutically effective amount or an artificial reproductive technology (ART).

10. The method according to claim 7, wherein the sperm function of said sample is quantified by determining the percentage of bound versus unbound sperm cells by microscopic analysis, or electrochemical detection.

11. The method according to claim 7, wherein the sperm function of said sample is quantified by determining the acrosomal status of the sperm cells in the semen sample by microscopic analysis or electrochemical detection.

12. A method of selecting sperm, said method comprising:
a) providing a semen sample from a subject, wherein said semen sample comprises one or more sperm cells,
b) contacting the semen sample with a biosensor comprising an Izumo sperm-egg fusion 1 receptor (JUNO) protein or a fragment thereof (first fragment) immobilized on a substrate, said substrate is a dish, a microbead, or an electrode, and wherein the JUNO protein or the first fragment, when immobilized on the substrate, binds a sperm, wherein at least a portion of the sperm comprises an IZUMO1 surface antigen,
c) visualizing a sperm cell bound to the biosensor by microscopy, and
d) selecting at least one sperm cell bound to the biosensor.

13. A method of manufacturing a biosensor that comprises (1) an Izumo sperm-egg fusion 1 receptor (JUNO) protein or a fragment thereof (first fragment) immobilized on a substrate which is a dish, a microbead, or an electrode, and the JUNO protein or the first fragment, and when immobilized on the substrate, binds a sperm, wherein at least a portion of the sperm comprises an IZUMO1, the method comprising:
a) immobilizing the JUNO protein or the first fragment on the substrate.

14. The method according to claim 13,
wherein the dish is coupled to a microscope or an optical transducer, or
wherein the microbead is coupled to a microscope, an optical transducer, or a measurement circuit, or
wherein the electrode is coupled to an electrochemical workstation or a measurement circuit.

15. A hand-held device for detection or quantification of sperm function, the device comprising:

a) an inlet for a sample,
b) a biosensor that comprises (1) an Izumo sperm-egg fusion 1 receptor (JUNO) protein or a fragment thereof (first fragment) immobilized on a substrate which is a dish, a microbead, or an electrode, and the JUNO protein or the first fragment, and when immobilized on the substrate, binds a sperm, wherein at least a portion of the sperm comprises an IZUMO1 surface antigen,
c) a detector configured to receive a signal from the substrate and transform it into a format readable by a user, and
d) optionally, means for separating cellular components from the sample.

16. The hand-held device according to claim 15,
wherein the dish is coupled to a microscope or an optical transducer; or
wherein the microbead is coupled to a microscope, an optical transducer, or a measurement circuit; or
wherein the electrode is coupled to an electrochemical workstation or a measurement circuit.

17. The method according to claim 7, wherein the biosensor further comprises Zona pellucida 1 (ZP1), Zona pellucida 2 (ZP2), Zona pellucida 3 (ZP3), an anti-IZUMO antibody, or a fragment of the ZP1, ZP2, ZP3, or the anti-IZUMO antibody (second fragment) immobilized on the substrate, said second fragment is capable of binding to a sperm or to IZUMO.

18. The method according to claim 8, wherein the biosensor further comprises Zona pellucida 1 (ZP1), Zona pellucida 2 (ZP2), Zona pellucida 3 (ZP3), an anti-IZUMO antibody, or a fragment of the ZP1, ZP2, ZP3, or the anti-IZUMO antibody (second fragment) immobilized on the substrate, said second fragment is capable of binding to a sperm or to IZUMO.

19. The method according to claim 12, wherein the biosensor further comprises Zona pellucida 1 (ZP1), Zona pellucida 2 (ZP2), Zona pellucida 3 (ZP3), an anti-IZUMO antibody, or a fragment of the ZP1, ZP2, ZP3, or the anti-IZUMO antibody (second fragment) immobilized on the substrate, said second fragment is capable of binding to a sperm or to IZUMO.

20. The method according to claim 1, wherein the biosensor further comprises Zona pellucida 1 (ZP1), Zona pellucida 2 (ZP2), Zona pellucida 3 (ZP3), an anti-IZUMO antibody, or a fragment of the ZP1, ZP2, ZP3, or the anti-IZUMO antibody (second fragment) immobilized on the substrate, said second fragment is capable of binding to a sperm or to IZUMO.

* * * * *

```
                        SEQUENCE LISTING

<160> NUMBER OF SEQ ID NOS: 5

<210> SEQ ID NO 1
<211> LENGTH: 250
<212> TYPE: PRT
<213> ORGANISM: Homo sapiens

<400> SEQUENCE: 1

Met Ala Cys Trp Trp Pro Leu Leu Glu Leu Trp Thr Val Met Pro
1               5                   10                  15

Thr Trp Ala Gly Asp Glu Leu Leu Asn Ile Cys Met Asn Ala Lys His
                20                  25                  30

His Lys Arg Val Pro Ser Pro Glu Asp Lys Leu Tyr Glu Glu Cys Ile
                35                  40                  45

Pro Trp Lys Asp Asn Ala Cys Cys Thr Leu Thr Thr Ser Trp Glu Ala
    50                  55                  60

His Leu Asp Val Ser Pro Leu Tyr Asn Phe Ser Leu Phe His Cys Gly
65                  70                  75                  80

Leu Leu Met Pro Gly Cys Arg Lys His Phe Ile Gln Ala Ile Cys Phe
                85                  90                  95

Tyr Glu Cys Ser Pro Asn Leu Gly Pro Trp Ile Gln Pro Val Gly Ser
                100                 105                 110

Leu Gly Trp Glu Val Ala Pro Ser Gly Gln Gly Glu Arg Val Val Asn
                115                 120                 125

Val Pro Leu Cys Gln Glu Asp Cys Glu Glu Trp Trp Glu Asp Cys Arg
    130                 135                 140

Met Ser Tyr Thr Cys Lys Ser Asn Trp Arg Gly Gly Trp Asp Trp Ser
145                 150                 155                 160

Gln Gly Lys Asn Arg Cys Pro Lys Gly Ala Gln Cys Leu Pro Phe Ser
                165                 170                 175

His Tyr Phe Pro Thr Pro Ala Asp Leu Cys Glu Lys Thr Trp Ser Asn
                180                 185                 190

Ser Phe Lys Ala Ser Pro Glu Arg Arg Asn Ser Gly Arg Cys Leu Gln
                195                 200                 205

Lys Trp Phe Glu Pro Ala Gln Gly Asn Pro Asn Val Ala Val Ala Arg
    210                 215                 220

Leu Phe Ala Ser Ser Ala Pro Ser Trp Glu Leu Ser Tyr Thr Ile Met
225                 230                 235                 240

Val Cys Ser Leu Phe Leu Pro Phe Leu Ser
                245                 250
```

<210> SEQ ID NO 2
<211> LENGTH: 638
<212> TYPE: PRT
<213> ORGANISM: Homo sapiens

<400> SEQUENCE: 2

```
Met Ala Gly Gly Ser Ala Thr Thr Trp Gly Tyr Pro Val Ala Leu Leu
1               5                   10                  15

Leu Leu Val Ala Thr Leu Gly Leu Gly Arg Trp Leu Gln Pro Asp Pro
            20                  25                  30

Gly Leu Pro Gly Leu Arg His Ser Tyr Asp Cys Gly Ile Lys Gly Met
        35                  40                  45

Gln Leu Leu Val Phe Pro Arg Pro Gly Gln Thr Leu Arg Phe Lys Val
    50                  55                  60

Val Asp Glu Phe Gly Asn Arg Phe Asp Val Asn Asn Cys Ser Ile Cys
65                  70                  75                  80

Tyr His Trp Val Thr Ser Arg Pro Gln Glu Pro Ala Val Phe Ser Ala
                85                  90                  95

Asp Tyr Arg Gly Cys His Val Leu Glu Lys Asp Gly Arg Phe His Leu
            100                 105                 110

Arg Val Phe Met Glu Ala Val Leu Pro Asn Gly Arg Val Asp Val Ala
        115                 120                 125

Gln Asp Ala Thr Leu Ile Cys Pro Lys Pro Asp Pro Ser Arg Thr Leu
    130                 135                 140

Asp Ser Gln Leu Ala Pro Pro Ala Met Phe Ser Val Ser Thr Pro Gln
145                 150                 155                 160

Thr Leu Ser Phe Leu Pro Thr Ser Gly His Thr Ser Gln Gly Ser Gly
                165                 170                 175

His Ala Phe Pro Ser Pro Leu Asp Pro Gly His Ser Ser Val His Pro
            180                 185                 190

Thr Pro Ala Leu Pro Ser Pro Gly Pro Gly Pro Thr Leu Ala Thr Leu
        195                 200                 205

Ala Gln Pro His Trp Gly Thr Leu Glu His Trp Asp Val Asn Lys Arg
    210                 215                 220

Asp Tyr Ile Gly Thr His Leu Ser Gln Glu Gln Cys Gln Val Ala Ser
225                 230                 235                 240

Gly His Leu Pro Cys Ile Val Arg Arg Thr Ser Lys Glu Ala Cys Gln
                245                 250                 255

Gln Ala Gly Cys Cys Tyr Asp Asn Thr Arg Glu Val Pro Cys Tyr Tyr
            260                 265                 270

Gly Asn Thr Ala Thr Val Gln Cys Phe Arg Asp Gly Tyr Phe Val Leu
        275                 280                 285

Val Val Ser Gln Glu Met Ala Leu Thr His Arg Ile Thr Leu Ala Asn
    290                 295                 300

Ile His Leu Ala Tyr Ala Pro Thr Ser Cys Ser Pro Thr Gln His Thr
305                 310                 315                 320

Glu Ala Phe Val Val Phe Tyr Phe Pro Leu Thr His Cys Gly Thr Thr
                325                 330                 335

Met Gln Val Ala Gly Asp Gln Leu Ile Tyr Glu Asn Trp Leu Val Ser
            340                 345                 350

Gly Ile His Ile Gln Lys Gly Pro Gln Gly Ser Ile Thr Arg Asp Ser
        355                 360                 365

Thr Phe Gln Leu His Val Arg Cys Val Phe Asn Ala Ser Asp Phe Leu
    370                 375                 380
```

```
Pro Ile Gln Ala Ser Ile Phe Pro Pro Ser Pro Ala Pro Met Thr
385                 390                 395                 400

Gln Pro Gly Pro Leu Arg Leu Glu Leu Arg Ile Ala Lys Asp Glu Thr
            405                 410                 415

Phe Ser Ser Tyr Tyr Gly Glu Asp Tyr Pro Ile Val Arg Leu Leu
        420                 425                 430

Arg Glu Pro Val His Val Glu Val Arg Leu Leu Gln Arg Thr Asp Pro
        435                 440                 445

Asn Leu Val Leu Leu His Gln Cys Trp Gly Ala Pro Ser Ala Asn
        450                 455                 460

Pro Phe Gln Gln Pro Gln Trp Pro Ile Leu Ser Asp Gly Cys Pro Phe
465                 470                 475                 480

Lys Gly Asp Ser Tyr Arg Thr Gln Met Val Ala Leu Asp Gly Ala Thr
            485                 490                 495

Pro Phe Gln Ser His Tyr Gln Arg Phe Thr Val Ala Thr Phe Ala Leu
        500                 505                 510

Leu Asp Ser Gly Ser Gln Arg Ala Leu Arg Gly Leu Val Tyr Leu Phe
        515                 520                 525

Cys Ser Thr Ser Ala Cys His Thr Ser Gly Leu Glu Thr Cys Ser Thr
530                 535                 540

Ala Cys Ser Thr Gly Thr Thr Arg Gln Arg Ser Ser Gly His Arg
545                 550                 555                 560

Asn Asp Thr Ala Arg Pro Gln Asp Ile Val Ser Ser Pro Gly Pro Val
            565                 570                 575

Gly Phe Glu Asp Ser Tyr Gly Gln Glu Pro Thr Leu Gly Pro Thr Asp
        580                 585                 590

Ser Asn Gly Asn Ser Ser Leu Arg Pro Leu Leu Trp Ala Val Leu Leu
        595                 600                 605

Leu Pro Ala Val Ala Leu Val Leu Gly Phe Gly Val Phe Val Gly Leu
        610                 615                 620

Ser Gln Thr Trp Ala Gln Lys Leu Trp Glu Ser Asn Arg Gln
625                 630                 635

<210> SEQ ID NO 3
<211> LENGTH: 745
<212> TYPE: PRT
<213> ORGANISM: Homo sapiens

<400> SEQUENCE: 3

Met Ala Cys Arg Gln Arg Gly Gly Ser Trp Ser Pro Ser Gly Trp Phe
1               5                   10                  15

Asn Ala Gly Trp Ser Thr Tyr Arg Ser Ile Ser Leu Phe Phe Ala Leu
            20                  25                  30

Val Thr Ser Gly Asn Ser Ile Asp Val Ser Gln Leu Val Asn Pro Ala
        35                  40                  45

Phe Pro Gly Thr Val Thr Cys Asp Glu Arg Glu Ile Thr Val Glu Phe
    50                  55                  60

Pro Ser Ser Pro Gly Thr Lys Lys Trp His Ala Ser Val Val Asp Pro
65                  70                  75                  80

Leu Gly Leu Asp Met Pro Asn Cys Thr Tyr Ile Leu Asp Pro Glu Lys
                85                  90                  95

Leu Thr Leu Arg Ala Thr Tyr Asp Asn Cys Thr Arg Arg Val His Gly
            100                 105                 110

Gly His Gln Met Thr Ile Arg Val Met Asn Asn Ser Ala Ala Leu Arg
```

```
            115                 120                 125
His Gly Ala Val Met Tyr Gln Phe Phe Cys Pro Ala Met Gln Val Glu
            130                 135                 140
Glu Thr Gln Gly Leu Ser Ala Ser Thr Ile Cys Gln Lys Asp Phe Met
145                 150                 155                 160
Ser Phe Ser Leu Pro Arg Val Phe Ser Gly Leu Ala Asp Asp Ser Lys
                165                 170                 175
Gly Thr Lys Val Gln Met Gly Trp Ser Ile Glu Val Gly Asp Gly Ala
            180                 185                 190
Arg Ala Lys Thr Leu Thr Leu Pro Glu Ala Met Lys Glu Gly Phe Ser
            195                 200                 205
Leu Leu Ile Asp Asn His Arg Met Thr Phe His Val Pro Phe Asn Ala
            210                 215                 220
Thr Gly Val Thr His Tyr Val Gln Gly Asn Ser His Leu Tyr Met Val
225                 230                 235                 240
Ser Leu Lys Leu Thr Phe Ile Ser Pro Gly Gln Lys Val Ile Phe Ser
                245                 250                 255
Ser Gln Ala Ile Cys Ala Pro Asp Pro Val Thr Cys Asn Ala Thr His
            260                 265                 270
Met Thr Leu Thr Ile Pro Glu Phe Pro Gly Lys Leu Lys Ser Val Ser
            275                 280                 285
Phe Glu Asn Gln Asn Ile Asp Val Ser Gln Leu His Asp Asn Gly Ile
            290                 295                 300
Asp Leu Glu Ala Thr Asn Gly Met Lys Leu His Phe Ser Lys Thr Leu
305                 310                 315                 320
Leu Lys Thr Lys Leu Ser Glu Lys Cys Leu Leu His Gln Phe Tyr Leu
                325                 330                 335
Ala Ser Leu Lys Leu Thr Phe Leu Leu Arg Pro Glu Thr Val Ser Met
            340                 345                 350
Val Ile Tyr Pro Glu Cys Leu Cys Glu Ser Pro Val Ser Ile Val Thr
            355                 360                 365
Gly Glu Leu Cys Thr Gln Asp Gly Phe Met Asp Val Glu Val Tyr Ser
            370                 375                 380
Tyr Gln Thr Gln Pro Ala Leu Asp Leu Gly Thr Leu Arg Val Gly Asn
385                 390                 395                 400
Ser Ser Cys Gln Pro Val Phe Glu Ala Gln Ser Gln Gly Leu Val Arg
                405                 410                 415
Phe His Ile Pro Leu Asn Gly Cys Gly Thr Arg Tyr Lys Phe Glu Asp
            420                 425                 430
Asp Lys Val Val Tyr Glu Asn Glu Ile His Ala Leu Trp Thr Asp Phe
            435                 440                 445
Pro Pro Ser Lys Ile Ser Arg Asp Ser Glu Phe Arg Met Thr Val Lys
            450                 455                 460
Cys Ser Tyr Ser Arg Asn Asp Met Leu Leu Asn Ile Asn Val Glu Ser
465                 470                 475                 480
Leu Thr Pro Pro Val Ala Ser Val Lys Leu Gly Pro Phe Thr Leu Ile
                485                 490                 495
Leu Gln Ser Tyr Pro Asp Asn Ser Tyr Gln Gln Pro Tyr Gly Glu Asn
            500                 505                 510
Glu Tyr Pro Leu Val Arg Phe Leu Arg Gln Pro Ile Tyr Met Glu Val
            515                 520                 525
Arg Val Leu Asn Arg Asp Asp Pro Asn Ile Lys Leu Val Leu Asp Asp
            530                 535                 540
```

```
Cys Trp Ala Thr Ser Thr Met Asp Pro Asp Ser Phe Pro Gln Trp Asn
545                 550                 555                 560

Val Val Val Asp Gly Cys Ala Tyr Asp Leu Asp Asn Tyr Gln Thr Thr
                565                 570                 575

Phe His Pro Val Gly Ser Ser Val Thr His Pro Asp His Tyr Gln Arg
            580                 585                 590

Phe Asp Met Lys Ala Phe Ala Phe Val Ser Glu Ala His Val Leu Ser
        595                 600                 605

Ser Leu Val Tyr Phe His Cys Ser Ala Leu Ile Cys Asn Arg Leu Ser
    610                 615                 620

Pro Asp Ser Pro Leu Cys Ser Val Thr Cys Pro Val Ser Arg His
625                 630                 635                 640

Arg Arg Ala Thr Gly Ala Thr Glu Ala Glu Lys Met Thr Val Ser Leu
                645                 650                 655

Pro Gly Pro Ile Leu Leu Ser Asp Asp Ser Ser Phe Arg Gly Val
            660                 665                 670

Gly Ser Ser Asp Leu Lys Ala Ser Gly Ser Ser Gly Glu Lys Ser Arg
        675                 680                 685

Ser Glu Thr Gly Glu Glu Val Gly Ser Arg Gly Ala Met Asp Thr Lys
    690                 695                 700

Gly His Lys Thr Ala Gly Asp Val Gly Ser Lys Ala Val Ala Val
705                 710                 715                 720

Ala Ala Phe Ala Gly Val Val Ala Thr Leu Gly Phe Ile Tyr Tyr Leu
                725                 730                 735

Tyr Glu Lys Arg Thr Val Ser Asn His
            740                 745

<210> SEQ ID NO 4
<211> LENGTH: 424
<212> TYPE: PRT
<213> ORGANISM: Homo sapiens

<400> SEQUENCE: 4

Met Glu Leu Ser Tyr Arg Leu Phe Ile Cys Leu Leu Leu Trp Gly Ser
1               5                   10                  15

Thr Glu Leu Cys Tyr Pro Gln Pro Leu Trp Leu Leu Gln Gly Gly Ala
            20                  25                  30

Ser His Pro Glu Thr Ser Val Gln Pro Val Leu Val Glu Cys Gln Glu
        35                  40                  45

Ala Thr Leu Met Val Met Val Ser Lys Asp Leu Phe Gly Thr Gly Lys
    50                  55                  60

Leu Ile Arg Ala Ala Asp Leu Thr Leu Gly Pro Glu Ala Cys Glu Pro
65                  70                  75                  80

Leu Val Ser Met Asp Thr Glu Asp Val Val Arg Phe Glu Val Gly Leu
                85                  90                  95

His Glu Cys Gly Asn Ser Met Gln Val Thr Asp Asp Ala Leu Val Tyr
            100                 105                 110

Ser Thr Phe Leu Leu His Asp Pro Arg Pro Val Gly Asn Leu Ser Ile
        115                 120                 125

Val Arg Thr Asn Arg Ala Glu Ile Pro Ile Glu Cys Arg Tyr Pro Arg
    130                 135                 140

Gln Gly Asn Val Ser Ser Gln Ala Ile Leu Pro Thr Trp Leu Pro Phe
145                 150                 155                 160

Arg Thr Thr Val Phe Ser Glu Glu Lys Leu Thr Phe Ser Leu Arg Leu
```

```
            165                 170                 175
Met Glu Glu Asn Trp Asn Ala Glu Lys Arg Ser Pro Thr Phe His Leu
            180                 185                 190

Gly Asp Ala Ala His Leu Gln Ala Glu Ile His Thr Gly Ser His Val
        195                 200                 205

Pro Leu Arg Leu Phe Val Asp His Cys Val Ala Thr Pro Thr Pro Asp
    210                 215                 220

Gln Asn Ala Ser Pro Tyr His Thr Ile Val Asp Phe His Gly Cys Leu
225                 230                 235                 240

Val Asp Gly Leu Thr Asp Ala Ser Ser Ala Phe Lys Val Pro Arg Pro
                245                 250                 255

Gly Pro Asp Thr Leu Gln Phe Thr Val Asp Val Phe His Phe Ala Asn
            260                 265                 270

Asp Ser Arg Asn Met Ile Tyr Ile Thr Cys His Leu Lys Val Thr Leu
        275                 280                 285

Ala Glu Gln Asp Pro Asp Glu Leu Asn Lys Ala Cys Ser Phe Ser Lys
    290                 295                 300

Pro Ser Asn Ser Trp Phe Pro Val Glu Gly Ser Ala Asp Ile Cys Gln
305                 310                 315                 320

Cys Cys Asn Lys Gly Asp Cys Gly Thr Pro Ser His Ser Arg Arg Gln
                325                 330                 335

Pro His Val Met Ser Gln Trp Ser Arg Ser Ala Ser Arg Asn Arg Arg
            340                 345                 350

His Val Thr Glu Glu Ala Asp Val Thr Val Gly Pro Leu Ile Phe Leu
        355                 360                 365

Asp Arg Arg Gly Asp His Glu Val Glu Gln Trp Ala Leu Pro Ser Asp
    370                 375                 380

Thr Ser Val Val Leu Leu Gly Val Gly Leu Ala Val Val Val Ser Leu
385                 390                 395                 400

Thr Leu Thr Ala Val Ile Leu Val Leu Thr Arg Arg Cys Arg Thr Ala
                405                 410                 415

Ser His Pro Val Ser Ala Ser Glu
            420

<210> SEQ ID NO 5
<211> LENGTH: 350
<212> TYPE: PRT
<213> ORGANISM: Homo sapiens

<400> SEQUENCE: 5

Met Gly Pro His Phe Thr Leu Leu Cys Ala Ala Leu Ala Gly Cys Leu
1               5                   10                  15

Leu Pro Ala Glu Gly Cys Val Ile Cys Asp Pro Ser Val Val Leu Ala
            20                  25                  30

Leu Lys Ser Leu Glu Lys Asp Tyr Leu Pro Gly His Leu Asp Ala Lys
        35                  40                  45

His His Lys Ala Met Met Glu Arg Val Glu Asn Ala Val Lys Asp Phe
    50                  55                  60

Gln Glu Leu Ser Leu Asn Glu Asp Ala Tyr Met Gly Val Val Asp Glu
65                  70                  75                  80

Ala Thr Leu Gln Lys Gly Ser Trp Ser Leu Leu Lys Asp Leu Lys Arg
                85                  90                  95

Ile Thr Asp Ser Asp Val Lys Gly Asp Leu Phe Val Lys Glu Leu Phe
            100                 105                 110
```

```
Trp Met Leu His Leu Gln Lys Glu Thr Phe Ala Thr Tyr Val Ala Arg
            115             120                 125

Phe Gln Lys Glu Ala Tyr Cys Pro Asn Lys Cys Gly Val Met Leu Gln
        130                 135                 140

Thr Leu Ile Trp Cys Lys Asn Cys Lys Lys Glu Val His Ala Cys Arg
145                 150                 155                 160

Lys Ser Tyr Asp Cys Gly Glu Arg Asn Val Glu Val Pro Gln Met Glu
                165                 170                 175

Asp Met Ile Leu Asp Cys Glu Leu Asn Trp His Gln Ala Ser Glu Gly
            180                 185                 190

Leu Thr Asp Tyr Ser Phe Tyr Arg Val Trp Gly Asn Asn Thr Glu Thr
        195                 200                 205

Leu Val Ser Lys Gly Lys Glu Ala Thr Leu Thr Lys Pro Met Val Gly
        210                 215                 220

Pro Glu Asp Ala Gly Ser Tyr Arg Cys Glu Leu Gly Ser Val Asn Ser
225                 230                 235                 240

Ser Pro Ala Thr Ile Ile Asn Phe His Val Thr Val Leu Pro Lys Met
            245                 250                 255

Ile Lys Glu Glu Lys Pro Ser Pro Asn Ile Val Thr Pro Gly Glu Ala
            260                 265                 270

Thr Thr Glu Ser Ser Ile Ser Leu Gln Pro Leu Gln Pro Glu Lys Met
        275                 280                 285

Leu Ala Ser Arg Leu Leu Gly Leu Leu Ile Cys Gly Ser Leu Ala Leu
        290                 295                 300

Ile Thr Gly Leu Thr Phe Ala Ile Phe Arg Arg Arg Lys Val Ile Asp
305                 310                 315                 320

Phe Ile Lys Ser Ser Leu Phe Gly Leu Gly Ser Gly Ala Ala Glu Gln
                325                 330                 335

Thr Gln Val Pro Lys Glu Lys Ala Thr Asp Ser Arg Gln Gln
            340                 345                 350
```